(12) United States Patent
Ropp et al.

(10) Patent No.: US 8,071,590 B2
(45) Date of Patent: Dec. 6, 2011

(54) 9-SUBSTITUTED-5-CARBOXY-OXADIAZINO-QUINOLONE DERIVATIVES, THEIR PREPARATION AND THEIR APPLICATION AS ANTI-BACTERIALS

(75) Inventors: Sandrine Ropp, Wolfisheim (FR);
Christophe Morice, Widensolen (FR);
Bruno Giethlen, Altorf (FR); Paola Ciapetti, Altorf (FR); Florence Chery-Mozziconacci, Strasbourg (FR);
Camille G. Wermuth, Strasbourg (FR);
Francoise Leblanc, Moffans (FR);
Marc Schneider, Lure (FR)

(73) Assignee: Vetoquinol SA, Lure (FR)

( * ) Notice: Subject to any disclaimer, the term of this patent is extended or adjusted under 35 U.S.C. 154(b) by 255 days.

(21) Appl. No.: 12/489,528

(22) Filed: Jun. 23, 2009

(65) Prior Publication Data

US 2010/0009980 A1    Jan. 14, 2010

Related U.S. Application Data

(60) Provisional application No. 61/098,413, filed on Sep. 19, 2008.

(30) Foreign Application Priority Data

Jul. 9, 2008   (EP) ..................................... 08290678

(51) Int. Cl.
C07D 498/06   (2006.01)
A61K 31/5365   (2006.01)
(52) U.S. Cl. ....................................... 514/229.2; 544/66
(58) Field of Classification Search ............. 544/66; 514/229.2
See application file for complete search history.

(56) References Cited

U.S. PATENT DOCUMENTS

| | | | |
|---|---|---|---|
| 4,649,144 A * | 3/1987 | Matsumoto et al. | |
| 4,801,584 A * | 1/1989 | Yokose et al. | |
| 4,990,517 A * | 2/1991 | Petersen et al. | |
| 5,354,747 A * | 10/1994 | Hansen et al. | |
| 5,480,879 A * | 1/1996 | Petersen et al. | |
| 5,508,278 A * | 4/1996 | Jaetsch et al. | |
| 5,576,314 A * | 11/1996 | Power et al. | |
| 5,679,675 A * | 10/1997 | Jaetsch et al. | |
| 6,284,757 B1 * | 9/2001 | Sanner | |
| 2003/0225107 A1 * | 12/2003 | Fukuda | |
| 2004/0110810 A1 * | 6/2004 | Ciufolini et al. | |
| 2005/0239852 A1 * | 10/2005 | Ciufolini et al. | |
| 2007/0142390 A1 * | 6/2007 | Moussy et al. | |
| 2008/0039466 A1 * | 2/2008 | Moussy et al. | |
| 2008/0255141 A1 * | 10/2008 | Ciufolini et al. | |
| 2009/0221565 A1 * | 9/2009 | Ropp et al. | |

FOREIGN PATENT DOCUMENTS

| EP | 0 259 804 | 3/1988 |
|---|---|---|
| EP | 0 394 553 | 3/1989 |
| EP | 0 343 524 | 11/1989 |
| EP | 0 470 252 | 4/1990 |
| EP | 0 647 644 | 8/1994 |
| EP | 0 682 030 | 4/1995 |
| EP | 0 688 772 | 6/1995 |
| EP | 1 182 202 | 2/2002 |
| WO | WO 97/27201 | 7/1997 |
| WO | WO 2004/005295 | 1/2004 |
| WO | WO 2004/096221 | 11/2004 |
| WO | WO 2005/026154 | 3/2005 |
| WO | WO 2006/027694 | 8/2005 |
| WO | WO 2006/072831 | 12/2005 |
| WO | WO 2006/044454 | 4/2006 |
| WO | WO 2007/011284 | 1/2007 |
| WO | WO 2007/021982 | 2/2007 |
| WO | WO 2007/085760 | 2/2007 |
| WO | WO 2007/028654 | 3/2007 |

OTHER PUBLICATIONS

Cain, James P. et al., "Design, synthesis, and biological evaluation of a new class of small molecule peptide mimetics targeting the menaocortin receptors," Bioorganic & Medicinal Chemistry Letters 16 (2006) pp. 5462-5467.

Cesare, P. Di. et al., "Fluoronaphthyridines and -quinolones as Antibacterial Agents. 5. Synthesis and Antimicrobial Actiivty of Chiral 1-tert-Butyl-6-fluoro-7-substituted-naphthyridones;" J. Med. Chem. 1992, vol. 35, pp. 4205-4213.

Dax, S.L. et al.: "Quinolone Antibacterials: A Hydroxymethylation—Intramolecular Cyclization Route To Pyrido [3,2,1-*ij*]-1,3,4-Benzoxadiazines;" J. Org. Chem., vol. 57, No. 2, 1992; pp. 744-746.

Falorni, Massimo et al., "Chiral Ligands Containing Heteroatoms. 15.1 Cyclic β-Amino Alcohols as Chiral Inductors for Enantioselective Reductions of Ketones," Tetrahedron: Asymmetry, vol. 7, No. 9, 1996, pp. 2739-2742.

(Continued)

*Primary Examiner* — Kahsay T Habte
(74) *Attorney, Agent, or Firm* — Harness, Dickey & Pierce, P.L.C.

(57) ABSTRACT

A subject of the invention is the compounds of formula (I):

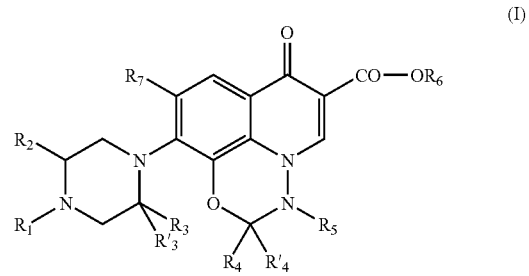

wherein $R_1$, $R_2$, $R_3$, $R'_3$, $R_4$, $R'_4$, $R_5$, $R_6$ and $R_7$ are as described in the application, in the form of enantiomers or mixtures, as well as their salts with acids and bases, their preparation and their application as anti-bacterials, in both human and veterinary medicine.

15 Claims, No Drawings

OTHER PUBLICATIONS

Falorni, Massimo et al., "Chiral Ligands Containing Heteroatoms. 11.1 Optically Active 2-Hydroxymethyl Piperazines as Catalysts in the Enantioselective Addition of Diethylzinc to Benzaidehyde," Tetrahedron: Asymmetry, vol. 4, No. 11, 1993, pp. 2389-2398.

Falorni, Massimo et al., "Synthesis of (2R,5S)- and (2S,5S)-2-Carboxy-1,4-diaza-[4.3.0]bicyclononane as Building Blocks for the Synthesis of New Potential HIV Protease Inhibitors," Tetrahedron: Asymmetry, vol. 7, No. 7, 1996, pp. 1999-2005.

Jain, Sanjay et al., Lactam & Amide Acetals XXI. Use of Pyroglutamic Acid and Proline in Chiral Synthesis of Conformationally Constrained Piperazinones, Tetrahedron vol. 48, No. 23, 1992, pp. 4985-4998.

Li, Qun et al., "Synthesis and Structure—Activity Relationships of 2-Pyridones: A Novel Series of Potent DNA Gyrase Inhibitors as Antibacterial Agents;" J. Med. Chem. 1996, vol. 39, pp. 3070-3088.

Peng, Hairuo et al., "Novel Bicyclic Piperazine Derivatives of Triazolotriazine and Triazolopyrimidines as Highly Potent and Selective Adenosine A2A Receptor Antagonists," J. Med. Chem. 2004, 47, Oct. 30, 2004, pp. 6218-6229.

Poumarat, F. et al.; "Mise Au Point Et Evaluation D'Une Methode Opacimetrique Pour La Determination De L'Antibiosensibilite De Mycoplasma Bovis In Vitro;" Ann, Rech. Vet. (20), 1989; pp. 135-143.

Scapecchi, Serena et al., "Structure-activity relationship studies on unifiram (DM232) and sunifiram (DM235), two novel and potent cognition enhancing drugs," Bioorganic & Medicinal Chemistry 12 (2004), pp. 71-85.

Snyder et al., PubMed Abstract (J. Med. Liban 48(4): 208-214, Jul.-Aug. 2000.

Tomita, Kyoji et al., "Synthesis and Structure—Activity Relationships of Novel 7-Substituted 1,4-Dihydro-4-oxo-1-(2-thiazolyl)-1,8-naphthyridine-3-carboxylic Acids as Antitumor Agents. Part 1," J. Med. Chem. 2002, vol. 45, pp. 5564-5575.

Tsuzuki, Yasunori et al., "Synthesis and Structure—Activity Relationships of Novel 7-Substituted 1,4-Dihydro-4-oxo-1-(2-thiazolyI)-1,8-naphthyridine-3-carboxylic Acids as Antitumor Agents. Part 2," J. Med. Chem. 2004, vol. 47, pp. 2097-2109.

* cited by examiner

9-SUBSTITUTED-5-CARBOXY-OXADIAZINO-QUINOLONE DERIVATIVES, THEIR PREPARATION AND THEIR APPLICATION AS ANTI-BACTERIALS

CROSS-REFERENCE TO RELATED APPLICATIONS

This application claims the benefit and priority to U.S. Provisional Application No. 61/098,413, filed on Sep. 19, 2008, and also claims benefit and priority to European Patent Application No. 08290678.5, filed on Jul. 9, 2008, both of which are incorporated herein by reference.

BACKGROUND AND SUMMARY

The subject of the invention is novel 9-substituted-5-carboxy-oxadiazino-quinolone derivatives, their preparation and their application as anti-bacterials.

9-substituted-5-carboxy-oxadiazino-quinolone derivatives have been described in various patents, applications or publications and there may be cited for example: EP 0259804, EP 0343524, EP 0688772, EP 0394553, EP 0470252, U.S. Pat. No. 4,990,517, U.S. Pat. No. 5,480,879, U.S. Pat. No. 5,679,675, or also J. Med. Chem. 1996, 39, 3070-3088, J. Med. Chem. 2002, 45, 5564-5575, or J. Med. Chem. 2004, 47, 2097-2109. In particular, EP 0394553 and EP 0470252 describe quinolone derivatives substituted by a piperazine ring bearing substituents which can form a spiro ring.

An object of the invention is the compounds of formula (I):

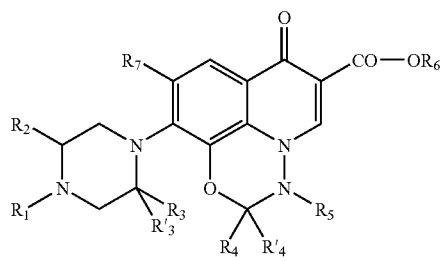

in which:
either $R_1$ and $R_2$ form a 5 or 6 membered carbon cycle optionally substituted by a group Ra and/or by two groups Rb and R'b fixed on the same carbon atom, Ra represents hydrogen, halogen, $(C_1-C_6)$ linear or branched alkyl, $(C_3-C_6)$ cyclic alkyl, $(C_6-C_{10})$ aryl, $(C_7-C_{12})$ aralkyl, OH, $(C_1-C_6)$ linear or branched alkoxy, O—$(C_6-C_{10})$ aryl, O—$(C_7-C_{12})$ aralkyl or NRR', R and R', represent together a $(C_3-C_6)$ carbon chain possibly interrupted by an heteroatom selected from N, O and S and optionally substituted by 1 or 2 $(C_1-C_6)$ linear or branched alkyls, or R and R', identical or different, represent hydrogen, $(C_1-C_6)$ linear or branched alkyl, $(C_3-C_6)$ cyclic alkyl or R represents hydrogen and R' represents a 5 or 6 membered heterocycle containing 1 to 3 heteroatoms selected from N, O and S, optionally substituted by 1 or 2 $(C_1-C_6)$ linear or branched alkyls, Rb and R'b, identical or different, represent hydrogen, $(C_1-C_6)$ linear or branched alkyl, $(C_3-C_6)$ cyclic alkyl, $(C_6-C_{10})$ aryl or $(C_7-C_{12})$ aralkyl, or Rb and R'b form together a carbonyl;

or $R_1$ represents a CO—$R'_1$ radical, wherein $R'_1$ represents a 5 or 6 membered heterocycle containing 1 to 3 heteroatoms selected from N, O and S, optionally substituted by 1 or 2 $(C_1-C_6)$ linear or branched alkyls, and $R_2$ represents hydrogen;

or $R_1$ represents a radical of formula:

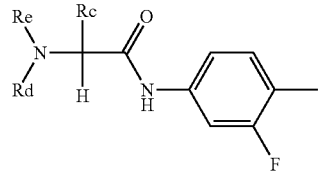

wherein Rc represents a $(C_1-C_6)$ linear or branched alkyl, optionally substituted by a member of the group constituted by COOH, COORf, $NH_2$, $NH(C_1-C_6)$ linear or branched alkyl, $N(C_1-C_6)$ di-linear or branched alkyl and NH—CO($C_1$-$C_6$) linear or branched alkyl, Rf represents a $(C_1-C_6)$ linear or branched alkyl, Rd represents hydrogen or CO—$(C_1-C_6)$ linear or branched alkyl and Re represents hydrogen, or Rc and Re form a pyrrolidine ring, and Rd is defined as above, and $R_2$ represents hydrogen;

or $R_1$ represents a radical of formula:

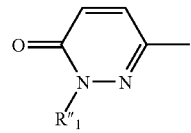

wherein $R''_1$ represents a $(C_1-C_6)$ linear or branched alkyl substituted by COOH, COORf, Rg or CORg, Rf is defined as above, Rg represents a morpholino, thiomorpholino or piperazino group possibly substituted by a $(C_1-C_6)$ linear or branched alkyl or Rg represents phenyl optionally substituted by 1 to 3 members of the group constituted by halogen, $CF_3$, $(C_1-C_6)$ linear or branched alkyl and $(C_1-C_6)$ linear or branched alkoxy, or Rg represents a 5 or 6 membered heterocycle containing 1 to 3 heteroatoms selected from N, O and S, optionally substituted by 1 or 2 $(C_1-C_6)$ linear or branched alkyls, and $R_2$ represents hydrogen;

$R_3$ represents hydrogen, —$(CH_2)_m$—NRR', —$(CH_2)_m$—OR, $(C_1-C_6)$ linear or branched alkyl, $(C_3-C_6)$ cyclic alkyl, or $R_3$ represents $(C_6-C_{10})$ aryl or $(C_7-C_{12})$ aralkyl or a 5 or 6 membered heterocycle containing 1 to 3 heteroatoms selected from N, O and S, all being possibly substituted by halogen, $CF_3$, $(C_1-C_6)$ linear or branched alkyl and $(C_1-C_6)$ linear or branched alkoxy, m is 0, 1 or 2 and R and R' are defined as above and $R'_3$ represents hydrogen, or $R_3$ and $R'_3$ represent $(C_1-C_6)$ linear or branched alkyl or form together a (C3-$C_6$) spiro ring;

$R_4$ and $R'_4$, identical or different, represent hydrogen or $(C_1-C_6)$ linear or branched alkyl optionally substituted by 1 to 3 halogens or $R_4$ represents a $(C_1-C_6)$ linear or branched alkoxy carbonyl group and $R'_4$ represents hydrogen;

$R_5$ represents methyl optionally substituted by one to three halogens;

$R_6$ represents hydrogen, $(C_1-C_6)$ linear or branched alkyl or $(C_7-C_{12})$ aralkyl;

$R_7$ represents hydrogen, fluorine, $NO_2$, $CF_3$ or CN;

in the form of mixtures of enantiomers or single enantiomers, as well as their addition salts with mineral and organic acids and their salts with mineral or organic bases.

The compounds of the invention have remarkable antibacterial properties which make them particularly indicated for use as medicaments in both human and veterinary medicine. In general formula (I) and hereafter:

by 5 or 6 membered heterocycle is meant an aromatic or non aromatic heterocycle and, for example, a pyrrole, furane, thiophene, pyrazole, triazole, tetrazole, thiazole, isothiazole, thiadiazole, imidazole, isoxazole, furazane, pyridine, pyrazine or pyridazine ring, the substituents being fixed, whenever possible, at any possible position, including on a nitrogen atom;

by $(C_1-C_6)$ linear or branched alkyl is meant any possible radical and in particular methyl, ethyl, propyl or isopropyl, butyl, isobutyl, tert-butyl or isopentyl;

by $(C_3-C_6)$ cyclic alkyl radical is meant any possible radical, cyclopropyl, cyclobutyl, cyclopentyl or cyclohexyl;

by linear or branched $(C_1-C_6)$ alkoxy is meant any possible radical and in particular methoxy, ethoxy, propoxy or isopropoxy, butoxy, isobutoxy or tert-butoxy;

by $(C_6-C_{10})$ aryl is meant phenyl or naphthyl, and preferably phenyl;

by $(C_7-C_{12})$ aralkyl is meant preferably benzyl or phenethyl;

the above aryl and aralkyl can be substituted by halogen, $CF_3$, $(C_1-C_6)$ linear or branched alkyl and $(C_1-C_6)$ linear or branched alkoxy;

by halogen in formula (I) and above is meant fluorine, chlorine, bromine or iodine, and preferably fluorine or chlorine.

Among the acid salts of the products of formula (I), there may be cited, among others, those formed with mineral acids, such as hydrochloric, hydrobromic, hydroiodic, sulphuric or phosphoric acid or with organic acids such as formic, acetic, trifluoroacetic, propionic, benzoic, maleic, fumaric, succinic, tartaric, citric, oxalic, glyoxylic, aspartic, alkanesulphonic acids, such as methanesulphonic and ethanesulphonic acids, arylsulphonic acids such as benzenesulphonic and paratoluenesulphonic acids. Among the base salts of the products of formula (I), there may be cited, among others, those formed with mineral alkalis such as, for example, sodium, potassium, lithium, calcium, magnesium or ammonium hydroxide or organic bases such as, for example, methylamine, propylamine, trimethylamine, diethylamine, triethylamine, N,N-dimethylethanolamine, tris(hydroxymethyl)aminomethane, ethanolamine, pyridine, piperidine, piperazine, picoline, dicyclohexylamine, morpholine, benzylamine, procaine, lysine, arginine, histidine, N-methylglucamine. Among the preferred compounds of formula (I) according to the invention are those wherein $R_4$, $R'_4$ and $R_6$ represent hydrogen, $R_5$ represents methyl, and $R_7$ represents fluorine.

A preferred object of the invention is the compounds of formula (I) as defined above, in which $R_1$ and $R_2$ form a 5 or 6 membered carbon cycle optionally substituted as defined above, $R_3$ and $R'_3$, $R_4$ and $R'_4$, $R_5$, $R_6$ and $R_7$ being defined as above, in the form of mixtures of enantiomers or single enantiomers, as well as their addition salts with mineral and organic acids and their salts with mineral or organic bases. An especially preferred object of the invention is the compounds of formula (I) as defined above, in which $R_1$ and $R_2$ form a 5 membered carbon cycle optionally substituted as defined above, $R_3$ and $R'_3$, $R_4$ and $R'_4$, $R_5$, $R_6$ and $R_7$ being defined as above, in the form of mixtures of enantiomers or single enantiomers, as well as their addition salts with mineral and organic acids and their salts with mineral or organic bases.

Within these preferred compounds one can especially mention those having the following formula $(I_1)$

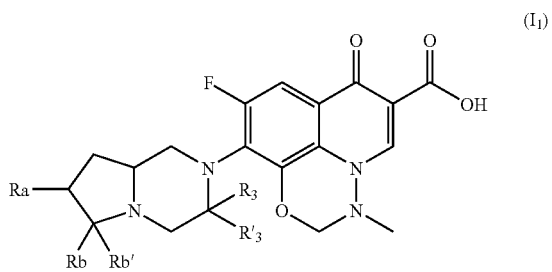

wherein Ra, Rb and R'b, $R_3$ and $R'_3$ are defined as above.

Another preferred object of the invention is the compounds of formula (I) as defined above, in which $R_1$ represents a CO—$R'_1$ radical, wherein $R'_1$ represents a 5 or 6 membered heterocycle containing 1 to 3 heteroatoms selected from N, O and S, optionally substituted by 1 or 2 $(C_1-C_6)$ linear or branched alkyls, and $R_2$ represents hydrogen, in the form of mixtures of enantiomers or single enantiomers, as well as their addition salts with mineral and organic acids and their salts with mineral or organic bases.

Another preferred object of the invention is the compounds of formula (I) as defined above, in which $R_1$ represents a radical of formula:

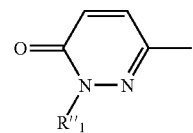

wherein $R''_1$ represents a $(C_1-C_6)$ linear or branched alkyl radical substituted by COOH, COORf, Rg or CORg, Rf represents a $(C_1-C_6)$ linear or branched alkyl, Rg represents morpholino, thiomorpholino or piperazino group, possibly substituted by a $(C_1-C_6)$ linear or branched alkyl radical or Rg represents phenyl optionally substituted by 1 to 3 members of the group constituted by halogen, $CF_3$, $(C_1-C_6)$ linear or branched alkyl and $(C_1-C_6)$ linear or branched alkoxy, or Rg represents a 5 or 6 membered heterocycle containing 1 to 3 heteroatoms selected from N, O and S, optionally substituted by 1 or 2 $(C_1-C_6)$ linear or branched alkyls, and $R_2$ represents hydrogen, in the form of mixtures of enantiomers or single enantiomers, as well as their addition salts with mineral and organic acids and their salts with mineral or organic bases.

Among the compounds of the invention, there may be cited the compounds described in the experimental part, in particular those whose names follow:

8-Fluoro-3-methyl-9-(octahydro-pyrido[1,2-a]pyrazin-2-yl)-6-oxo-2,3-dihydro-6H-1-oxa-3,3a-diaza-phenalene-5-carboxylic acid, 8-Fluoro-9-(hexahydro-pyrrolo[1,2-a]pyrazin-2-yl)-3-methyl-6-oxo-2,3-dihydro-6H-1-oxa-3,3a-diaza-phenalene-5-carboxylic acid, 8-Fluoro-9-(S)-hexahydro-pyrrolo[1,2-a]pyrazin-2-yl-3-methyl-6-oxo-2,3-dihydro-6H-1-oxa-3,3a-diaza-phenalene-5-carboxylic acid, 8-Fluoro-9-(R)-hexahydro-pyrrolo[1,2-a]pyrazin-2-yl-3-methyl-6-oxo-2,3-dihydro-6H-1-oxa-3,3a-diaza-phenalene-5-carboxylic acid, 8-Fluoro-3-methyl-9-[4-(1-methyl-1H-pyrrole-2-carbonyl)-piperazin-1-yl]-6-oxo-2,3-dihydro-6H-1-oxa-3,3a-diaza-phenalene-5-carboxylic acid, 8-Fluoro-3-methyl-6-oxo-9-[4-(2,3-dihydro-thiazole-4-carbonyl)-piperazin-1-yl]-2,3-dihydro-6H-1-oxa-3,3a-diaza-phenalene-5-carboxylic acid, 8-Fluoro-3-methyl-9-[4-(4-methyl-thiazole-5-carbonyl)-piperazin-1-yl]-6-oxo-2,3-dihydro-6H-1-oxa-3,3a-diaza-phenalene-5-carboxylic acid, 8-Fluoro-3-methyl-6-oxo-9-[4-(thiophene-2-carbonyl)-piperazin-1-yl]-2,3-dihydro-6H-1-oxa-3,3a-diaza-phenalene-5-carboxylic acid, 8-Fluoro-9-[4-(furan-2-carbonyl)-piperazin-1-yl]-3-methyl-6-oxo-2,3-dihydro-6H-1-oxa-3,3a-diaza-phenalene-5-carboxylic acid, 8-Fluoro-3-methyl-9-{4-[1-(2-morpholin-4-yl-ethyl)-6-oxo-1,6-dihydro-pyridazin-3-yl]-piperazin-1-yl}-6-oxo-2,3-dihydro-6H-1-oxa-3,3a-diaza-phenalene-5-carboxylic acid, 8-Fluoro-9-{4-[1-(3-methoxy-benzyl)-6-oxo-1,6-dihydro-pyridazin-3-yl]-piperazin-1-yl}3-methyl-6-oxo-2,3-dihydro-6H-1-oxa-3,3a-diaza-phenalene-5-carboxylic acid, as well as their salts.

The compounds of the invention can be prepared by a method characterized in that a compound of formula (II):

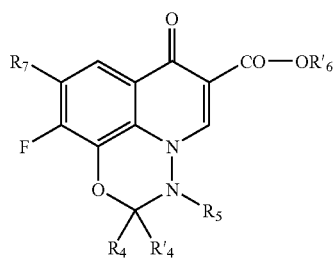

(II)

in which $R_4$, $R'_4$, $R_5$ and $R_7$ are as defined above and $R'_6$ has the values of $R_6$ defined above or represents another group protecting the carboxylic function, is treated by a compound of formula (III):

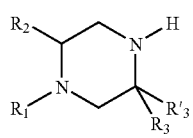

(III)

in which $R_1$, $R_2$, $R_3$ and $R'_3$ are as previously defined, in the presence of a base, then, if appropriate, the protective groups present are eliminated and, if desired, the carboxy group is esterified by action of an alcohol, and the compound of formula (I) is salified.

The procedure is carried out preferably in a sealed chamber, in solution in the pyridine, at the reflux temperature of the latter. The base used is preferably a tertiary amine, for example triethylamine, N-methyl morpholine or also DBU. When $R'_6$ represents a protective group, it can in particular be a ($C_1$-$C_6$) alkyl, a ($C_2$-$C_6$) alkenyl, or a ($C_7$-$C_{14}$) arylalkyl. After final elimination of the protective group $R'_6$, the acid obtained can if desired be re-esterified to form a compound in which $R_6$ is different from hydrogen.

Protection of the heterocyclic nitrogen and the amines may be necessary and is carried out in particular, according to circumstances, in the form of benzyl or trityl derivatives, in the form of carbamates, in particular allyl, benzyl, phenyl or tertbutyl, or also in the form of silyl derivatives such as dimethyl, trimethyl, triphenyl tertbutyl or also diphenyl tertbutyl-silyl derivatives. Deprotection is carried out, according to the nature of the protective group, by sodium or lithium in liquid ammonia, by hydrogenolysis or using soluble palladium 0 complexes, by action of an acid, or by action of tetrabutylammonium fluoride or strong bases such as sodium hydride or potassium tert-butylate. These reactions are well known to a person skilled in the art and well described for example by T. W. Green, P. G. M. Wuts, Protective Groups in Organic Synthesis, Wiley-Interscience, New York. Illustrations are provided below in the experimental part.

The compounds of formula (II) are generally known and can be prepared by the methods described in U.S. Pat. No. 4,801,584. The compound of formula (II) in which $R_4$ and/or $R'_4$ represent/s an alkyl radical optionally substituted by 1 to 3 halogens can be prepared from a compound of formula (II) in which $R_4$ and $R'_4$ represent a hydrogen, which is hot-treated with an alkaline aqueous base, then neutralized, in order to obtain the compound of formula (IV):

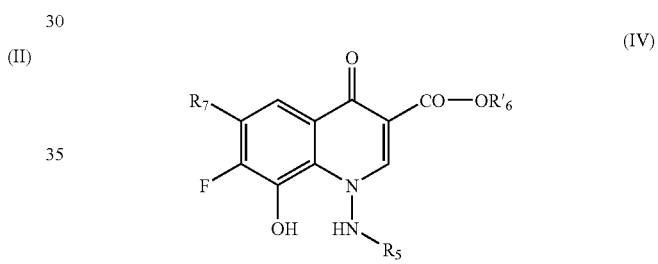

(IV)

in which $R_5$, $R'_6$ and $R_7$ are defined as above, which is treated in dioxane at boiling point by a compound of formula (V)

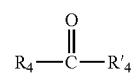

(V)

in which $R_4$ and $R'_4$ are defined as above. The compound of formula (II) in which R5 represents a methyl radical substituted by 1 to 3 halogens can be prepared according to a method such as the one described in U.S. Pat. No. 4,801,584.

The compounds of formula (III) can be prepared by methods known to the skilled chemist and, for example, by those described in the following documents: Helv. Chem. Acta, 1951, 12, 34, 1544-1575; J. Med. Chem. 2004, 47, 25, 6218-6229; Bioorg. Med. Chem. 2006, 16, 20, 5462-5467; Tetrahedron 1992, 48, 23, 4985-4998; Tetrahedron Asymmetry 1993, 4, 11, 2389-2398; Tetrahedron Asymmetry 1996, 7, 9, 2739-2742; Tetrahedron Assymetry 1993, 7, 7, 1999-2006; Bioorg. Med. Chem. Letters 2004, 12, 1, 71-86; WO2006127694; U.S. Pat. No. 6,284,757; WO2006172831; WO2007/28654; U.S. Pat. Nos. 5,354,747; 5,576,314. Preparations of compounds of formula (III) are also provided below in the experimental part.

Typically, following compounds of formula (IIIa):

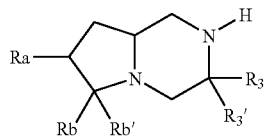

(IIIa)

in which $R_3$, $R_3'$, Ra, Rb and Rb' are defined as above, can be prepared from a compound of formula (IV):

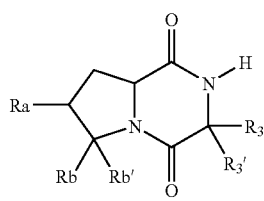

(IV)

which is treated by a strong reducer, preferentially $LiAlH_4$, in an ethereal solvent such as diethyl ether or tetrahydrofuran, at reflux temperature.

Compounds of formula (IV) can themselves be prepared by heating a compound of formula (V):

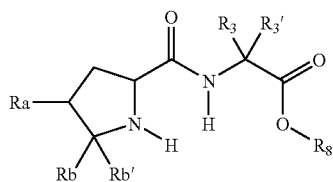

(V)

in which $R_8$ represents a $(C_1-C_6)$ alkyl or a $(C_7-C_{14})$ arylalkyl group, in an appropriated solvent, preferentially an alcoholic solvent such as methanol or ethanol.

Compounds of formula (V) can be prepared by coupling the appropriated substituted proline of formula (VI), in which Ra, Rb and Rb' are defined as above, with the corresponding amino ester of formula (VII) in which $R_3$, $R_3'$ and $R_8$ are defined as above.

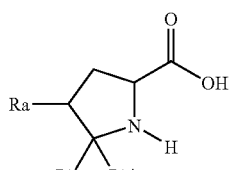

(VI)

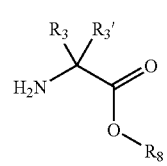

(VII)

The conditions for the coupling reaction are those known in the art, and can employ conventional associations of coupling reagents used in peptidic chemistry such as HOBT, EDCl, in presence of a base such as diisopropylethylamine or triethylamine and in a solvent such as dimethylformamide. Compounds of formula (III)/(IIIa), wherein $R_1$ and $R_2$ form a 5 or 6 membered carbon cycle are known and described for example in U.S. Pat. No. 5,354,257 or 5,576,314 and/or are commercially available. As stated above, the compounds of formula (I) can be in the form of enantiomers or mixtures of enantiomers essentially at position 9 of the ring. The compounds of formula (I) are obtained without racemization and, as a result, enantiomers can be obtained by using the corresponding enantiomer of the compound of formula (III) and/or (IV).

The compounds according to the invention, and more particularly those wherein $R_1$ and $R_2$ form an optionally substituted 5 or 6 membered carbon cycle, have remarkable antibacterial properties and these properties manifest themselves over a wide spectrum of gram (−) bacteria, but also a wide spectrum of gram (+). This balanced antibacterial activity distinguishes them from compounds of the prior art, for example marbofloxacine or also ofloxacine, and means that they are particularly indicated for use as medicaments in human medicine, but also in veterinary medicine for which there is a need for compounds which are particularly active in relation to these bacteria. Thus the above compounds are active in particular on gram (+) bacteria such as *Streptococcus uberis* or *Staphylococcus aureus*, but also *Mycoplasma bovis* or *bovirhinis*, or *Clostridium perfringens* or *Enterococcus faecalis*, while still being remarkably active on gram (−) bacteria such as *Mannheimia haemolytica, Bordetella bronchiseptica, Escherichia coli* or *Pseudomonas aeruginosa*.

These properties make said compounds, as well as their salts with pharmaceutically acceptable acids and bases, suitable for use as medicaments in the treatment of conditions with susceptible germs and in particular those involving staphylococci, such as staphylococcal septicaemia, malignant staphylococcal infection of the face or skin, pyoderma, septic or suppurating sores, anthrax, phlegmon, erysipeles, primitive or post-influenzal acute staphylococcal infections, bronchial pneumonia, pulmonary suppurations. The compounds can also be used as medicaments in the treatment of colibacilloses and associated infections, in *Proteus, Klebsiella, Pseudomonas* or also *Salmonella* infections and in other conditions caused by gram (−) bacteria.

A further subject of the present invention is therefore the use as medicaments, and in particular as antibiotic medicaments, of the compounds of formula (I) as defined above, as well as their salts with pharmaceutically acceptable acids and bases. More particularly, a subject of the invention is the use, as medicaments, of the preferred compounds of formula (I) defined above, in particular including the compounds of formula ($I_1$) defined above and the compounds listed below:

8-Fluoro-3-methyl-9-(octahydro-pyrido[1,2-a]pyrazin-2-yl)-6-oxo-2,3-dihydro-6H-1-oxa-3,3a-diaza-phenalene-5-carboxylic acid, 8-Fluoro-9-(hexahydro-pyrrolo[1,2-a]pyrazin-2-yl)-3-methyl-6-oxo-2,3-dihydro-6H-1-oxa-3,3a-diaza-phenalene-5-carboxylic acid, 8-Fluoro-9-(S)-hexahydro-pyrrolo[1,2-a]pyrazin-2-yl-3-methyl-6-oxo-2,3-dihydro-6H-1-oxa-3,3a-diaza-phenalene-5-carboxylic acid, 8-Fluoro-9-(R)-hexahydro-pyrrolo[1,2-a]pyrazin-2-yl-3-methyl-6-oxo-2,3-dihydro-6H-1-oxa-3,3a-diaza-phenalene-5-carboxylic acid, 8-Fluoro-3-methyl-9-[4-(1-methyl-1H-pyrrole-2-carbonyl)-piperazin-1-yl]-6-oxo-2,3-dihydro-6H-1-oxa-3,3a-diaza-phenalene-5-carboxylic acid, 8-Fluoro-3-methyl-6-oxo-9-[4-(2,3-dihydro-thiazole-4-carbonyl)-piperazin-1-yl]-2,3-dihydro-6H-1-oxa-3,3a-diazaphenalene-5-carboxylic acid, 8-Fluoro-3-methyl-9-[4-(4-methyl-thiazole-5-carbonyl)-piperazin-1-yl]-6-oxo-2,3-dihydro-6H-1-oxa-3,3a-diazaphenalene-5-carboxylic acid, 8-Fluoro-3-methyl-6-oxo-9-[4-(thiophene-2-carbonyl)-piperazin-1-yl]-2,3-dihydro-6H-1-oxa-3,3a-diaza-phenalene-5-carboxylic acid, 8-Fluoro-9-[4-(furan-2-carbonyl)-piperazin-1-yl]-3-methyl-6-oxo-2,3-dihydro-6H-1-oxa-3,3a-diaza-phenalene-5-carboxylic acid, 8-Fluoro-3-methyl-9-{4-[1-(2-morpholin-4-yl-ethyl)-6-oxo-1,6-dihydro-pyridazin-3-yl]-piperazin-1-yl}-6-oxo-2,3-dihydro-6H-1-oxa-3,3a-diaza-phenalene-5-carboxylic acid, 8-Fluoro-9-{4-[1-(3-methoxy-benzyl)-6-oxo-1,6-dihydro-pyridazin-3-yl]-piperazin-1-yl}-3-methyl-6-oxo-2,3-dihydro-6H-1-oxa-3,3a-diaza-phenalene-5-carboxylic acid, as well as their pharmaceutically acceptable salts.

A subject of the invention is also the pharmaceutical compositions containing, as active ingredient, at least one of the medicaments according to the invention as defined above. These compositions can be administered by oral, rectal, parenteral, in particular intramuscular route, by respiratory route or by local route in topical application to the skin and mucous membranes.

The compositions according to the invention can be solid or liquid and be present in the pharmaceutical forms commonly used in human medicine, such as for example, plain or sugar-coated tablets, gelatin capsules, granules, suppositories, injectable preparations, ointments, creams, gels; they are prepared according to the customary methods. The active ingredients can be incorporated in same, using excipients which are customarily used in these pharmaceutical compositions, such as talc, gum arabic, lactose, starch, magnesium stearate, cocoa buffer, aqueous or non-aqueous vehicles, fatty substances of animal or vegetable origin, paraffin derivatives, glycols, various wetting agents, dispersants or emulsifiers, preservatives. These compositions can in particular be present in the form of a powder intended to be dissolved extemporaneously in an appropriate vehicle, for example, non-pyrogenic sterile water. The dose administered varies according to the condition treated, the patient in question, the administration route and the product envisaged. It can, for example, be comprised between 0.25 g and 10 g per day, by oral route in humans, with the product described in example 1 or also comprised between 0.25 g and 10 g per day by intramuscular or intravenous route.

DETAILED DESCRIPTION

The following examples illustrate the invention.
In the following examples and, if applicable, in the description above, the abbreviations of chemical names have the following meanings:

| | |
|---|---|
| EDCI: | 1-(3-dimethylaminopropyl)-3-ethylcarbodiimide, |
| HOBt: | 1-hydroxybenzotriazole, |
| DBU: | 1,8-diaza-bicyclo-[5.4,0]-undec-7-ene, |
| TNOC: | 8,9-difluoro-3-methyl-6-oxo-2,3,3a,6-tetrahydronaphtho[1,8-de][1.3]oxazine-5-carboxylic acid, |
| ACN: | acetonitrile, |
| THF: | tetrahydrofurane, |
| DMF: | dimethylformamide, |
| LiHMDS: | lithium-hexamethyldisilylazide, |
| DMAP: | dimethylaminopyridine, |
| DEAD: | diéthyl azadicarboxylate, |
| PPh3: | triphenylphosphine, |
| TFA: | trifluroacetic acid, |
| Boc: | tert-butoxycarbonyl, |
| CBz: | benzyloxycarbonyl, |
| MS: | mass spectrum, |
| ESI$^+$: | positive ion electrospray ionization. |

NMR: The spectra were determined on spectrometers of the 300 or 400 MHz type, the proton and carbon spectra being respectively recorded at 300 and 75 MHz or 400 and 100 MHz, in solution in CDCl$_3$, or DMSO-d$_6$, MeOH-d$_4$. The values recorded are expressed in δ (ppm) and represent the s, d, t, quad, dd and m values. The constant J$_{AB}$ is expressed in Hz. Unless otherwise indicated, the reactions are carried out under dry inert gas and at ambient temperature.

"General method A" (coupling) consists of reacting the product "TNOC" (1.0 equivalent) and the aminated derivative in suspension in pyridine (0.2M) in a sealed chamber overnight at 120° C. under stirring. The solvent is evaporated off and toluene and/or methanol are added. After concentration to dryness, the crude product is triturated in methanol and separated then dried.

"General method B" (Boc deprotection) consists of adding a large excess of TFA to a solution in dichloromethane at 0° C. of protected amino derivative (N-Boc). The reaction is carried out at ambient temperature and followed by chromatography over silica. The solution is concentrated to dryness and toluene and/or methanol are added followed by evaporation. The crude product is obtained in the form of a trifluoroacetate.

"General method C" (peptide coupling) consists of adding 1.2 to 2.0 equivalents of EDCl and 1.2 to 2.0 equivalents of HOBt or DMAP and 1.2 to 2.0 equivalents of heteroaryl carboxylic acid, at 0° C., to a 0.2 to 0.6M solution within DMF of protected amino(piperidine) derivative N-Boc or N-CBz. The mixture is maintained under stirring at ambient temperature for 16 to 18 hours, then diluted with ethyl acetate and washed with water. The solution is then dried and concentrated to dryness under reduced pressure, then the residue is purified by chromatography over silica eluting with the cyclohexane-ethyl acetate mixture.

"General method D" (coupling reaction) consists of mixing 8,9-Difluoro-3-methyl-6-oxo-2.3,3a,6-tetrahydronaphto[1,8-de][1,3]oxazine-5-carboxylic acid "TNOC" (1.0 eq.) and a piperazine derivative (2.0 eq) and adding 1-methyl-2-pyrrolidinone. N,O-bis(trimethylsilyl)acetamide (1.0 eq.) and N-methylmorpholine (2.2 to 3.6 eq). The mixture was submitted to microwaves for half an hour to one hour at 120° C. or was heated at 95° C. for 6 to 8 hours. The reaction was cooled to 0° C. and water was added, the precipitate was filtered and washed with water. The solid was triturated with methanol or ethanol.

"General method E" (hydrogenation) consists of adding Pd/C to a solution of the piperazine derivative in a mixture of dichloromethane/methanol (0/41 to 1/1). The reaction mixture was submitted to hydrogenation at atmospheric pressure and room temperature or 30° C. for 1 to 24 hours. The mixture was filtrated over Celite® and evaporated under reduced pressure.

General Scheme for the Examples I to V:

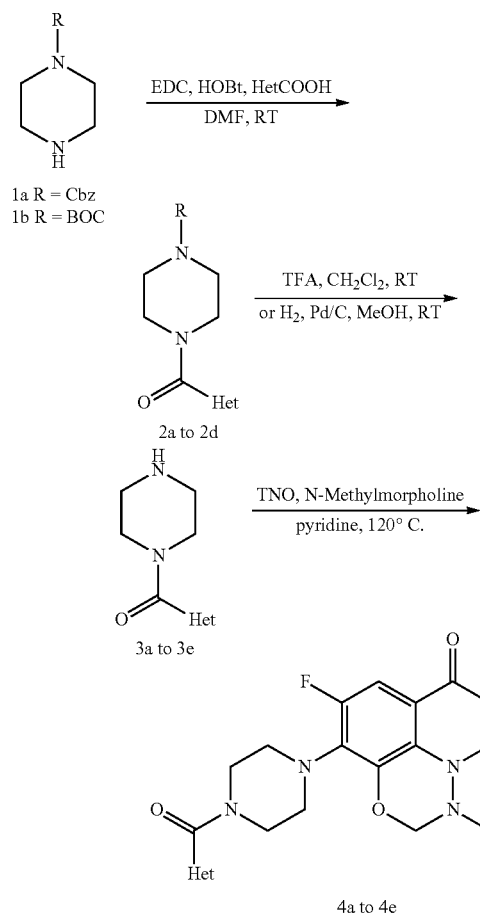

2a 3a 4a   R = Cbz, Het = 1-methyl-1-H-pyrrol-2-yl
2b 3b 4b   R = BOC, Het = thiazol-4-yl
2c 3c 4c   R = BOC, Het = 4-methyl-thiazol-5-yl
2d 3d 4d   R = BOC, Het = thiophen-2-yl
   3e 4e   Het = furan-2-yl

EXAMPLE I

Preparation of 8-Fluoro-3-methyl-9-[4-(1-methyl-1H-pyrrole-2-carbonyl)-piperazin-1-yl]-6-oxo-2,3-dihydro-6H-1-oxa-3,3a-diaza-phenalene-5-carboxylic acid (4a)

Step A: Preparation of 2a

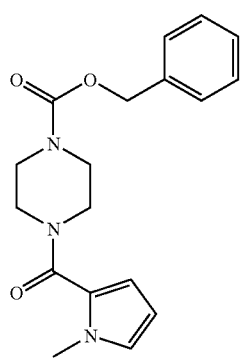

According to general procedure C, 2a was obtained with 1a (0.25 mL, 5.18 mmol, 1.0 eq.), EDC (324 mg, 10.36 mmol, 2.0 eq.), DMAP (317 mg, 10.36 mmol, 2.0 eq.) and N-methylpyrrole-2-carboxylic acid (329 mg, 10.36 mmol, 2.0 eq.). The mixture was washed first with a saturated solution of ammonium chloride, then with 1 N HCl and at the end with a saturated solution of sodium carbonate. The residue was purified by flash chromatography on silica gel, eluting with cyclohexane-ethyl acetate (8:2 to 1:1) to afford 2a (420 mg, 98%) as a colorless oil.

MS (ESI+) (+0.1% HCOOH): 328.12 $[C_{18}H_{21}N_3O_3+H]^+$ (m/z)

Step B: Preparation of 3a

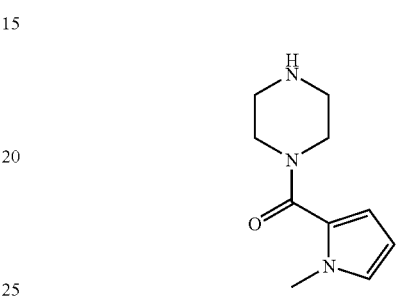

According to general procedure E, 2a (2.0 g, 6.11 mmol, 1.0 eq) was deprotected in methanol (20 mL) with palladium on activated carbon 10% (250 mg). The mixture was submitted to hydrogenation at room temperature under 1 atmosphere for 6 hours. The reaction mixture was filtered through Celite® and evaporated. The residue was purified by flash chromatography on silica gel, eluting with eluting with dichloromethane—7N $NH_3$ methanol (gradient from 5% to 20% methanol). The title compound was obtained as a colorless gum (1.1 g, 93%).

MS (ESI+) (+0.1% HCOOH): 194.09 $[C_{10}H_{15}N_3O+H]^+$ (m/z)

Step C: Preparation of 4a

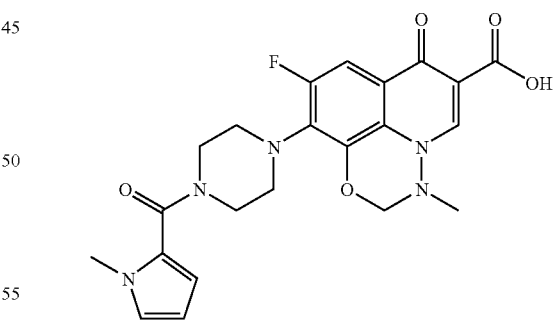

According to general procedure A, TNOC (535 mg, 1.89 mmol, 1.0 eq.) was coupled with 3a (1.1 g, 5.21 mmol, 3.0 eq.) and 1 mL of N-methylmorpholine. The residue was triturated several times with hot methanol to afford the title compound as a beige solid (321 mg, 37%).

HPLC (gradient 5%-80% ACN in $H_2O$): >99%

MS (ESI+) (+0.1% HCOOH): 456.1 $[C_{22}H_{22}FN_5O_5+H]^+$ (m/z)

mp=252° C. dec.

EXAMPLE II

Preparation of 9-[4-(2,3-Dihydro-thiazole-4-carbonyl)-piperazin-1-yl]-8-fluoro-3-methyl-6-oxo-2,3-dihydro-6H-1-oxa-3,3a-diaza-phenalene-5-carboxylic acid (4b)

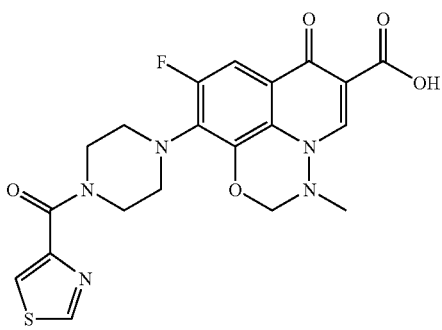

Step A: Preparation of 2b

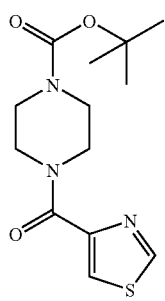

According to general procedure C, 2b was obtained with 1b (1.2 g, 6.45 mmol, 1.0 eq.), EDC (1.5 g, 7.25 mmol, 1.2 eq.), HOBt (1.1 g, 7.25 mmol, 1.2 eq.) and 4-thiazolecarboxylic acid (1.0 g, 7.25 mmol, 1.2 eq.). The mixture was washed first with a saturated solution of ammonium chloride, with 1N HCl, with a saturated solution of sodium bicarbonate and at the end water. The residue 2b (1.8 g, 94%) was used in the next step without further purification.

Step B: Preparation of 3b

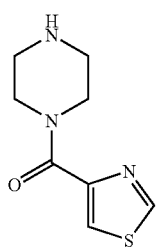

According to general procedure B, 2b (1.8 g, 6.05 mmol, 1.0 eq.) was deprotected; the residue was purified by flash chromatography on silica gel, eluting with eluting with dichloromethane—5% 7N NH$_3$ methanol to afford 3b (1.16 g, 97%).

MS (ESI+) (+0.1% HCOOH): 198.12 $[C_8H_{11}N_3OS+H]^+$ (m/z)

Step C: Preparation of 4b

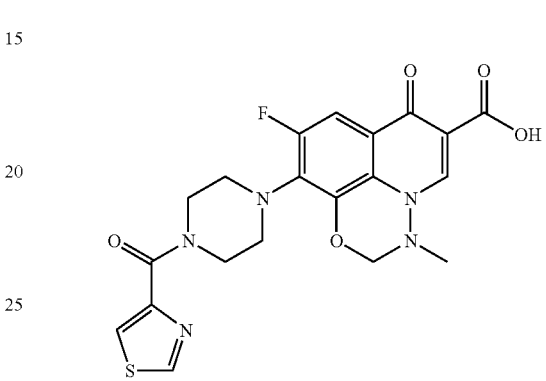

According to general procedure A, TNOC (524 mg, 1.86 mmol, 1.0 eq.) was coupled with 3b (1.1 g, 5.60 mmol, 3.0 eq.) and N-methylmorpholine (0.41 mL, mmol, 2.0 eq.). The residue was triturated first with water then with hot methanol to afford the title compound as a white solid (450 mg, 53%).

HPLC (gradient 5%-80% ACN in H$_2$O): >99%

MS (ESI+) (+0.1% HCOOH): 460.1 $[C_{20}H_{18}FN_5O_5+H]^+$ (m/z)

mp=311° C. dec.

EXAMPLE III

Preparation of 8-Fluoro-3-methyl-9-[4-(4-methyl-thiazole-5-carbonyl)-piperazin-1-yl]-6-oxo-2,3-dihydro-6H-1-oxa-3,3a-diaza-phenalene-5-carboxylic acid (4c)

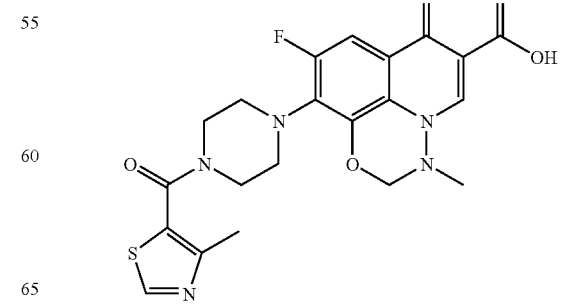

Step A: Preparation of 2c

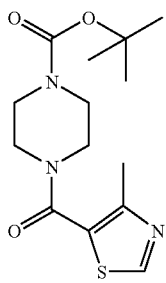

According to general procedure C, 2c was obtained with 1b (1.3 g, 6.98 mmol, 1.0 eq.), EDC (1.6 g, 8.37 mmol, 1.2 eq.), HOBt (1.1 g, 8.37 mmol, 1.2 eq.) and 4-methyl-thiazole-5-carboxylic acid (1.0 g, 6.78 mmol, 1.0 eq.). The mixture was washed water; the residue was purified by flash chromatography on silica gel, eluting with eluting with dichloromethane-methanol (gradient from 2.5% to 5% methanol). to afford 2c (1.6 g, 24%).

MS (ESI+) (+0.1% HCOOH): 312.09 $[C_{14}H_{21}N_3O_3S+H]^+$ (m/z)

Step B: Preparation of 3c

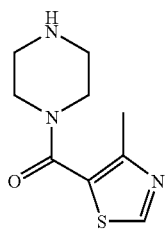

According to general procedure B, 2c (1.6 g, 5.14 mmol, 1.0 eq.) was deprotected; the residue was purified by flash chromatography on silica gel, eluting with eluting with dichloromethane—10% methanol then dichloromethane—7N NH$_3$ in methanol (gradient from 10% to 20% of 7N NH$_3$ in methanol) to afford 3c as a white wax (1.0 g, 92%).

MS (ESI+) (+0.1% HCOOH): 212.12 $[C_9H_{13}N_3OS+H]^+$ (m/z)

Step C: Preparation of 4c

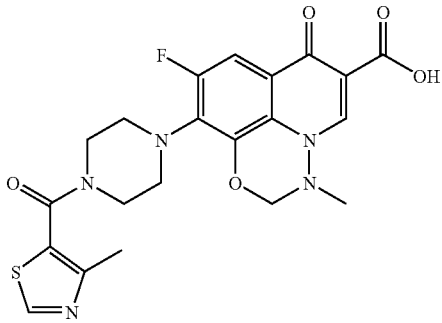

According to general procedure A, TNOC (600 mg, 2.12 mmol, 1.0 eq.) was coupled with 3c (1.0 g, 4.25 mmol, 2.2 eq.) and 1 mL of N-methylmorpholine. The residue was triturated with hot methanol to afford the title compound as a beige solid (302 mg, 27%).

HPLC (gradient 5%-80% ACN in H$_2$O): >99%

MS (ESI+) (+0.1% HCOOH): 425.0 $[C_{21}H_{20}FN_5O_5S+H]^+$ (m/z)

mp=285° C. dec.

EXAMPLE IV

Preparation of 8-Fluoro-3-methyl-6-oxo-9-[4-(thiophene-2-carbonyl)-piperazin-1-yl]-2,3-dihydro-6H-1-oxa-3,3a-diaza-phenalene-5-carboxylic acid (4d)

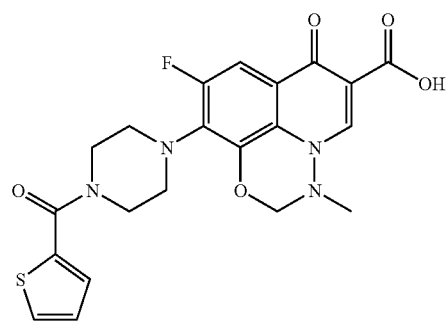

Step A: Preparation of 2d

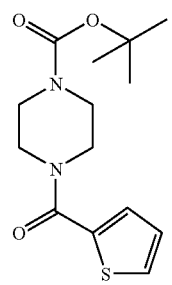

According to general procedure C, 2d was obtained with 1b (1.0 g, 5.35 mmol, 1.0 eq.), EDC (1.59 g, 8.03 mmol, 1.5 eq.), HOBt (1.09 g, 8.03 mmol, 1.5 eq.) and 2-thiophenecarboxylic acid (1.03 g, 8.03 mmol, 1.5 eq.). The mixture was washed first with a saturated solution of ammonium chloride, with 1N HCl, with a saturated solution of sodium bicarbonate and at the end water; the residue was purified by flash chromatography on silica gel, eluting with eluting with dichloromethane-methanol (gradient from 0% to 5% methanol). to afford 2d (1.5 g, 95%).

Step B: Preparation of 3d

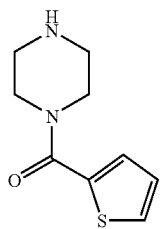

According to general procedure B, 2d (1.5 g, 5.06 mmol, 1.0 eq.) was deprotected; the residue was purified by flash chromatography on silica gel, eluting with eluting dichloromethane—5% 7N NH₃ in methanol to afford 3d (1.1 g, quantitative).
MS (ESI+) (+0.1% HCOOH): 197.2 $[C_9H_{12}N_2OS+H]^+$ (m/z)

Step C: Preparation of 4d

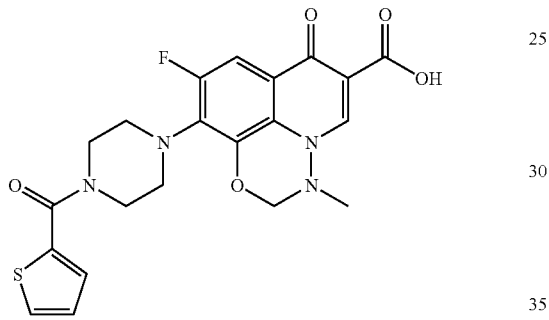

According to general procedure A, TNOC (524 mg, 1.86 mmol, 1.0 eq.) was coupled with 3d (1.1 g, 5.60 mmol, 3.0 eq.) and N-methylmorpholine (0.41 mL, mmol, 2.0 eq.). The residue was triturated first with water then with hot methanol to afford the title compound as a white solid (450 mg, 53%).
HPLC (gradient 5%-80% ACN in H₂O): >99%
MS (ESI+) (+0.1% HCOOH): 459.1 $[C_{21}H_{19}FN_4O_5S+H]^+$ (m/z)
mp=249° C. dec.

EXAMPLE V

Preparation of 8-Fluoro-9-[4-(furan-2-carbonyl)-piperazin-1-yl]-3-methyl-6-oxo-Z 3-dihydro-6H-1-oxa-3,3a-diaza-phenalene-5-carboxylic acid (4e)

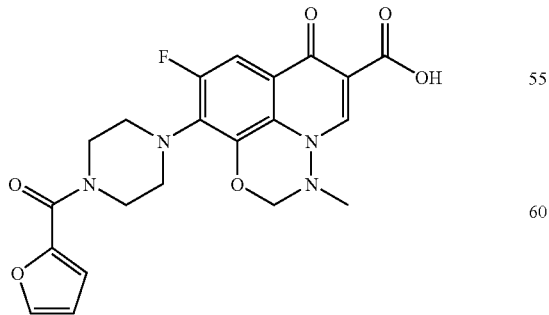

According to general procedure A, TNOC (200 mg, 0.22 mmol, 1.0 eq.) was coupled with 3e (639 mg, 3.55 mmol, 5.0 eq.). The residue was triturated with hot methanol to afford the title compound as a beige solid (136 mg, 43%).
HPLC (gradient 5%-80% ACN in H₂O): >95%
MS (ESI+) (+0.1% HCOOH): 443.0 $[C_{21}H_{19}FN_4O_6+H]^+$ (m/z)
mp=261° C.

General Scheme for the Examples VI to XII:

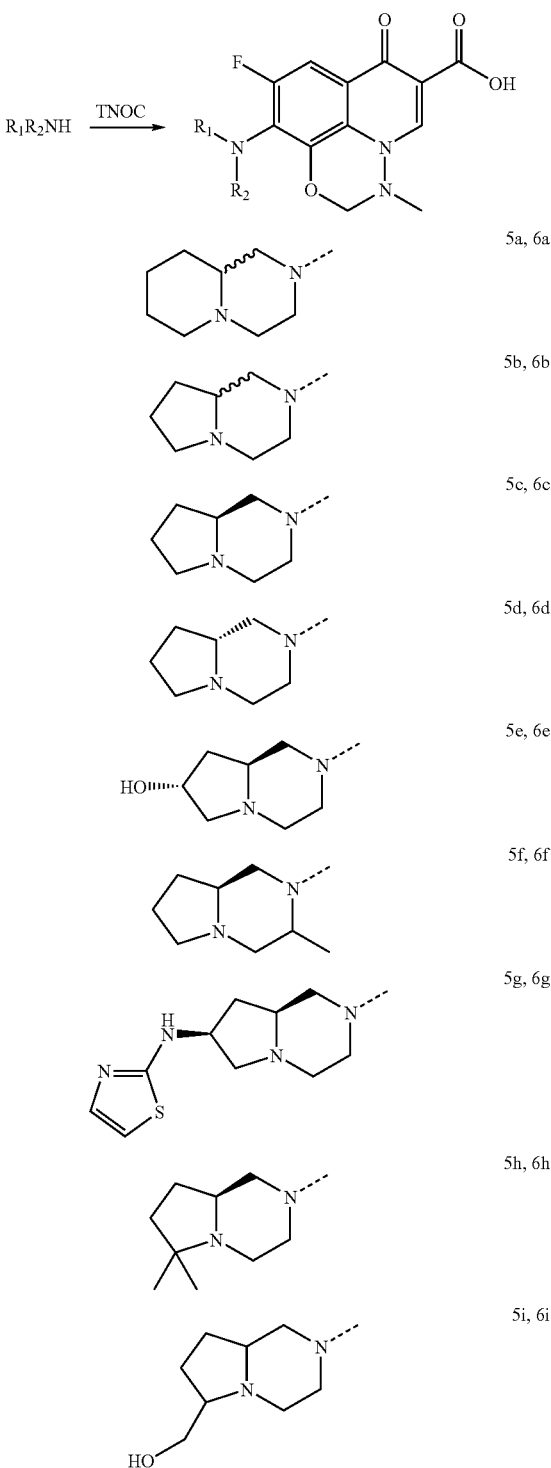

-continued

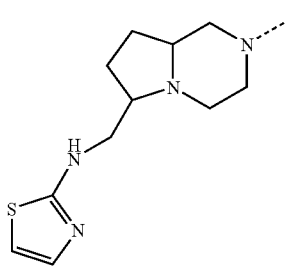

5j, 6j

EXAMPLE VI

Preparation of 8-Fluoro-3-methyl-9-(octahydro-pyrido[1,2-a]pyrazin-2-yl)-6-oxo-2,3-dihydro-6H-1-oxa-3,3a-diaza-phenalene-5-carboxylic acid (6a)

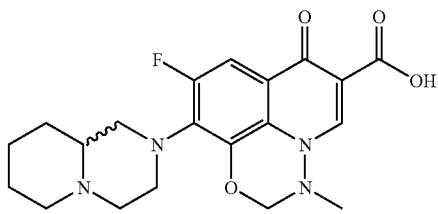

According to general procedure A, TNOC (599 mg, 2.12 mmol, 1.0 eq.) was coupled with 5a {Hansen et al. U.S. Pat. No. 5,354,747} (1.5 g, 8.49 mmol, 4.0 eq.) in 10 mL of pyridine and triethylamine (2.95 mL, 21.2 mmol, 10.0 eq.). The reaction was evaporated under reduced pressure, the residue was triturated with water, filtrated and the solid was washed with methanol to afford the title compound as a beige solid (325 mg, 24%)

HPLC (gradient 5% to 95% ACN in $H_2O$): >95%
MS ($ESI^+$) (+0.1% HCOOH): 403.3 $[C_{20}H_{23}FN_4O_4+H]^+$ (m/z)
mp=260-261° C., dec.

EXAMPLE VII

Preparation of 8-Fluoro-9-(hexahydro-pyrrolo[1,2-a]pyrazin-2-yl)-3-methyl-6-oxo-2,3-dihydro-6H-1-oxa-3,3a-diaza-phenalene-5-carboxylic acid (6b)

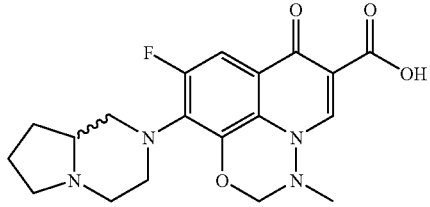

According to general procedure A, TNOC (559 mg, 1.98 mmol, 1.0 eq.) was coupled with 5b (octahydro-pyrrolo[1,2-a]pyrazine, commercially available) (1.0 g, 7.92 mmol, 4.0 eq.) in 10 mL of pyridine and N-methylmorpholine (0.435 mL, 3.96 mmol, 2.0 eq.). The reaction was evaporated under reduced pressure, the residue was triturated with methanol and filtrated to afford the title compound as a beige solid (480 mg, 62%)

HPLC (gradient 5% to 80% ACN in $H_2O$): >95%
MS ($ESI^+$) (+0.1% HCOOH): 389.23 $[C_{19}H_{21}FN_4O_4+H]^+$ (m/z)
mp=215° C., dec.

EXAMPLE VIII

Preparation of 8-Fluoro-9-(S)-hexahydro-pyrrolo[1,2-a]pyrazin-2-yl-3-methyl-6-oxo-2,3-dihydro-6H-1-oxa-3,3a-diaza-phenalene-5-carboxylic acid (6c)

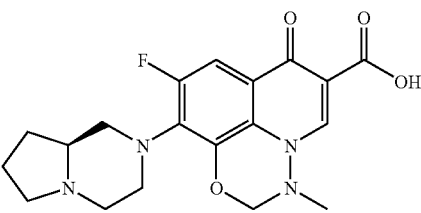

According to general procedure A, TNOC (161 mg, 2.31 mmol, 1.0 eq.) was coupled with 5c as a hydrochloride salt {Power et al. U.S. Pat. No. 5,576,314} (1.5 g, 7.57 mmol, 3.3 eq.) in 10 mL of pyridine and triethylamine (3.22 mL, 23.1 mmol, 10.0 eq.). The reaction was evaporated under reduced pressure, the residue was triturated with water, methanol, dichloromethane and at last with methanol to afford the title compound as a beige solid (213 mg, 24%)

HPLC (gradient 5% to 95% ACN in $H_2O$): >95%
MS ($ESI^+$) (+0.1% HCOOH): 389.3 $[C_{19}H_{21}FN_4O_4+H]^+$ (m/z)
mp=267° C., dec.

EXAMPLE IX

Preparation of 8-Fluoro-9-(R)-hexahydro-pyrrolo[1,2-a]pyrazin-2-yl-3-methyl-6-oxo-2,3-dihydro-6H-1-oxa-3,3a-diaza-phenalene-5-carboxylic acid (6d)

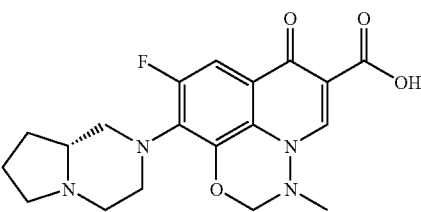

According to general procedure A, TNOC (161 mg, 2.31 mmol, 1.0 eq.) was coupled with 5d as a hydrochloride salt {Power et al. U.S. Pat. No. 5,576,314} (1.5 g, 7.57 mmol, 3.3 eq.) in 10 mL of pyridine and triethylamine (3.22 mL, 23.1 mmol, 10.0 eq.). The reaction was evaporated under reduced pressure; the residue was triturated with water, methanol, dichloromethane and at last with methanol to afford the title compound as a beige solid (280 mg, 31%)

HPLC (gradient 5% to 95% ACN in $H_2O$): >90%
MS ($ESI^+$) (+0.1% HCOOH): 389.2 $[C_{19}H_{21}FN_4O_4+H]^+$ (m/z)
mp=263° C., dec.

EXAMPLE X

8-Fluoro-9-((7R,8aS)-7-hydroxy-hexahydro-pyrrolo[1,2-a]pyrazin-2-yl)-5-hydroxymethyl-3-methyl-2,3-dihydro-1-oxa-3,3a-diaza-phenalen-6-one (6e)

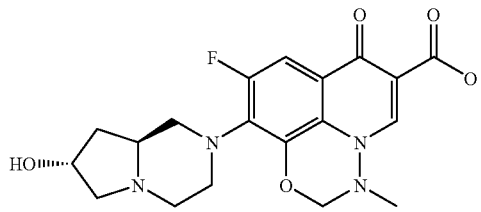

Step A: Preparation of 5e

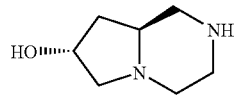

Following the procedure described by Power et al. compound 5e was obtained starting from (2S,4R)-4-hydroxy-pyrrolidine-1,2-dicarboxylic acid-1-tert-butyl ester instead of (2S)-pyrrolidine-1,2-dicarboxylic acid-1-tert-butyl ester in for steps in 39% overall yield.

Step B: preparation of 6e

TNOC (110 mg, 0.39 mmol, 1.0 eq.) was coupled with 5e (165 mg, 1.16 mmol, 3.0 eq.) in presence of DABCO (100 mg, 0.89 mmol, 2.3 eq.) and in 1 mL of pyridine and 2 ml of acetonitrile. The reaction mixture was stirred at 90° C. for 8 hours and then the precipitate was filtered and washed with acetonitrile and diethyl ether to afford the title compound as a brown solid (90 mg, 57%)

HPLC (gradient 5% to 95% ACN in H$_2$O): >95%

MS (ESI+) (+0.1% HCOOH): 405.2 [C$_{19}$H$_{21}$FN$_4$O$_5$+H]$^+$ (m/z)

mp=270° C.-272° C.

EXAMPLE XI

8-Fluoro-3-methyl-9-((S)-3-methyl-hexahydro-pyrrolo[1,2-a]pyrazin-2-yl)-6-oxo-2,3-dihydro-6H-1-oxa-3, 3a-diaza-phenalene-5-carboxylic acid (60

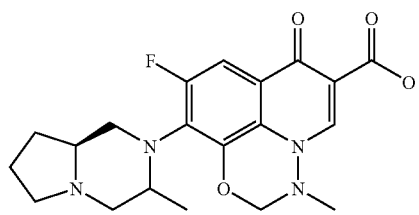

Step A: Preparation of 5f

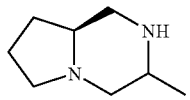

Following the procedure described by Power et al. compound 5f was obtained starting from DL-alanine methyl ester hydrochloride instead of glycine methyl ester hydrochloride in for steps in 3% overall yield.

Step B: preparation of 6f

According to general procedure A, TNOC (200 mg, 0.71 mmol, 1.0 eq.) was coupled with 5f (325 mg, 2.32 mmol, 3.3 eq.) in 3 mL of pyridine and N-methylmorpholine (0.16 mL, 1.45 mmol, 2.0 eq.). The reaction was evaporated under reduced pressure. The residue was purified on Sephadex LH-20 and then by T.L.C preparative to afford the title compound as a yellow solid (22 mg, 7%).

HPLC (gradient 5% to 95% ACN in H$_2$O): >95%

MS (ESI$^+$) (+0.1% HCOOH): 389.2 [C$_{20}$H$_{23}$FN$_4$O$_4$+H]$^+$ (m/z)

mp=185° C.-187° C.

General Scheme for Example XII:

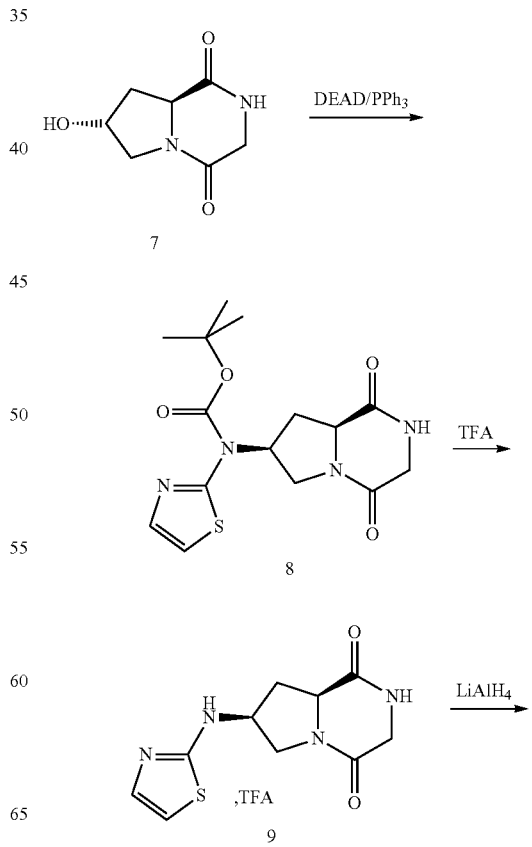

-continued

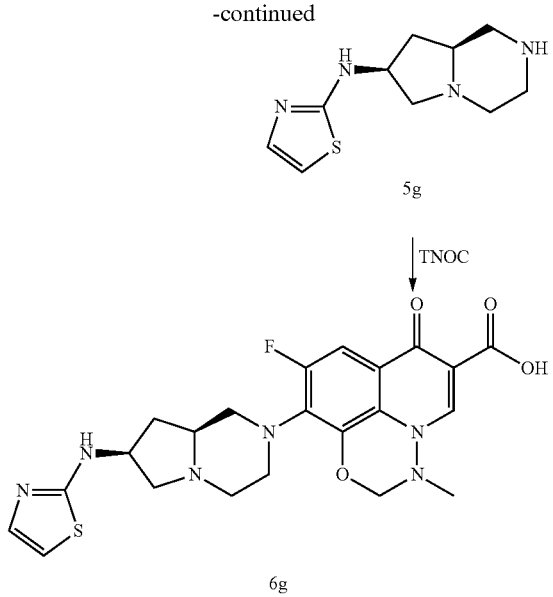

5g

6g

EXAMPLE XII

8-Fluoro-3-methyl-6-oxo-9-[(7S,8aS)-7-(thiazol-2-ylamino)-hexahydro-pyrrolo[1,2-a]pyrazin-2-yl]-2,3-dihydro-6H-1-oxa-3,3a-diaza-phenalene-5-carboxylic acid (6g)

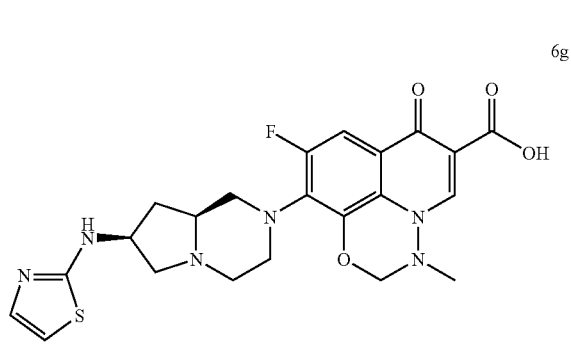

6g

Step A: Preparation of 8

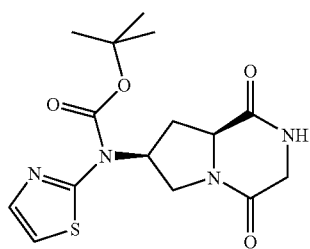

To a suspension of compound 7 (obtained as an intermediate during the synthesis of 5e) (810 mg, 4.76 mmol, 1.5 eq.) in THF (15 mL) at 0° C. were added successively PPh$_3$ (1.3 g, 4.96 mmol, 1.5 eq.), DEAD (2.2 mL, 4.80 mmol, 1.5 eq.) and Boc-aminothiazole (640 mg, 3.20 mmol, 1.0 eq.). The reaction mixture was stirred at room temperature for 18 hours. The reaction mixture was concentrated under reduced pressure and the resulting crude product was purified by flash chromatography on silica gel, eluting with dichloromethane-methanol (100:0 to 95:5) to afford 8 (990 mg, 88%) as a beige foam.

Step B: Preparation of 9

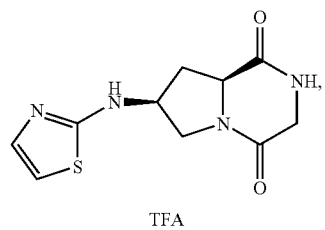

TFA

According to general procedure B, 8 (970 mg, 2.75 mmol, 1.0 eq.) was deprotected; the reaction was concentrated under reduced pressure and co-evaporated with methanol to afford 9 (1.1 g, quantitative) as a beige foam.

Step C: Preparation of 5g

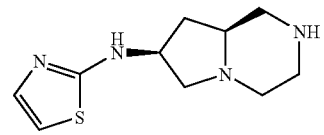

To a suspension of LiAlH$_4$ (200 mg, 5.27 mmol, 4.0 eq.) in THF (2 mL) at 0° C. was added dropwise a solution of compound 9 (500 mg, 1.36 mmol, 1.0 eq.) in THF (3 mL). The reaction mixture was stirred at 70° C. for 1 hour and half. The reaction was cooled to 0° C. and H$_2$O (0.2 mL), 5N NaOH (0.2 mL) and H$_2$O (0.1 mL) were added. The resulting mixture was filtered, the precipitate washed with dichloromethane and the filtrate was concentrated under reduced pressure to afford 5g (270 mg, 88%) as a beige oil.

Step D: Preparation of 6g

TNOC (110 mg, 0.39 mmol, 1.0 eq.) was coupled with 5g (260 mg, 1.16 mmol, 3.0 eq.) in presence of DABCO (90 mg, 0.80 mmol, 2.0 eq.) and in 0.5 mL of pyridine and 1 ml of acetonitrile. The reaction mixture was stirred at 90° C. for 6 hours and then the mixture was concentrated under reduced pressure and co-evaporated with methanol. The resulting crude product was purified by flash chromatography on silica gel, eluting with dichloromethane-methanol (1:0 to 9:1) to afford 6g (50 mg, 26%) as a yellow solid.

HPLC (gradient 5% to 95% ACN in H$_2$O): >90%

MS (ESI$^+$) (+0.1% HCOOH): 487.3 [C$_{22}$H$_{23}$FN$_6$O$_4$S+H]$^+$ (m/z)

mp=234° C.-236° C.

General Scheme for Example XIII:

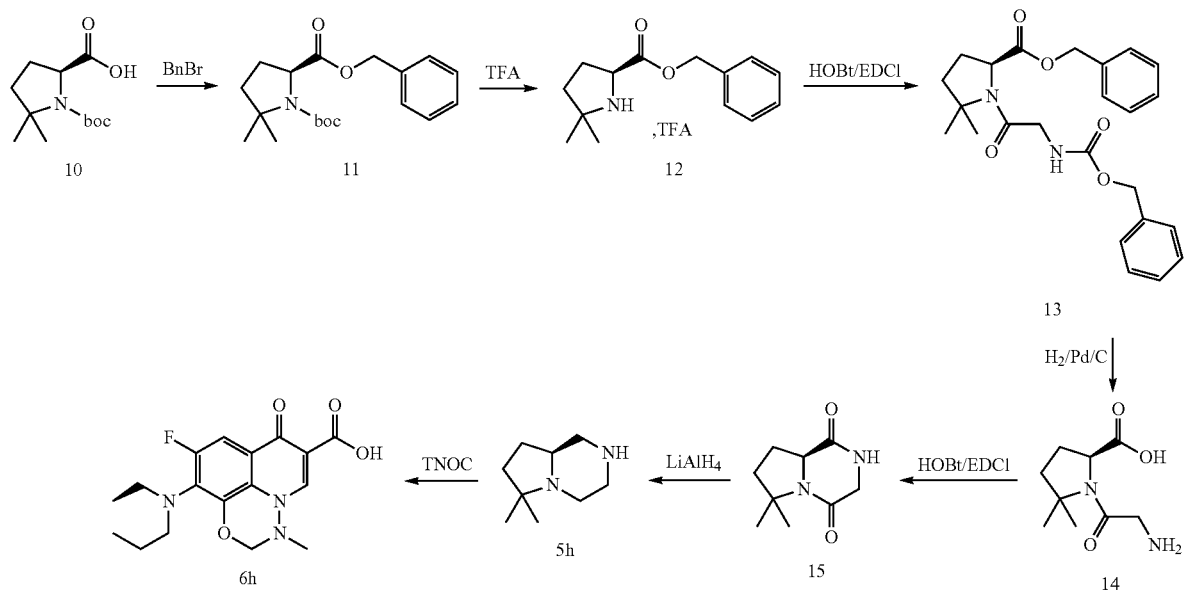

EXAMPLE XIII

8-Fluoro-3-methyl-6-oxo-9-((S)-6,6-Dimethyl-hexahydro-pyrrolo[1,2-a]pyrazin-2-yl)-2,3-dihydro-6H-1-oxa-3,3a-diaza-phenalene-5-carboxylic acid (6h)

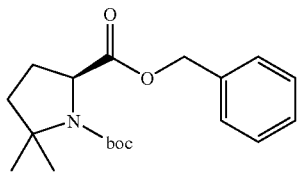

Step A: Preparation of 11

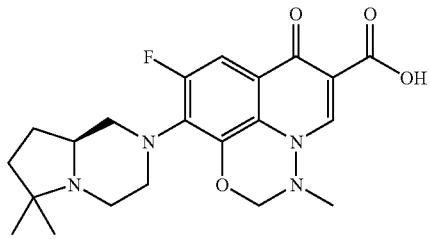

To a solution of (S)-Boc-5,5-dimethylproline (480 mg, 1.97 mmol, 1.0 eq.) in DMF (10 mL) at 0° C. was added $K_2CO_3$ (550 mg, 3.98 mmol, 2.0 eq.). The reaction mixture was stirred at 0° C. for 30 min and then benzyl bromide (0.3 mL, 2.53 mmol, 1.3 eq.) was added. The reaction mixture was stirred at room temperature for 3 hours. The reaction was diluted with EtOAc, the organic phase was washed with water. The organic extracts were dried over $Na_2SO_4$ and concentrated. The crude product was purified by flash chromatography on silica gel, eluting with cyclohexane-EtOAc (100:0 to 95:5) to afford 11 (710 mg, quantitative) as a colorless liquid.

Step B: Preparation of 12

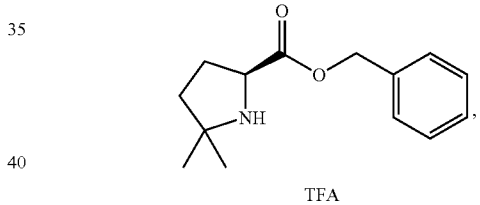

According to general procedure B, 11 (700 mg, 1.97 mmol, 1.0 eq.) was deprotected; the reaction was concentrated under reduced pressure and co-evaporated with methanol to afford 12 (880 mg, quantitative) as a colorless oil.

Step C: Preparation of 13

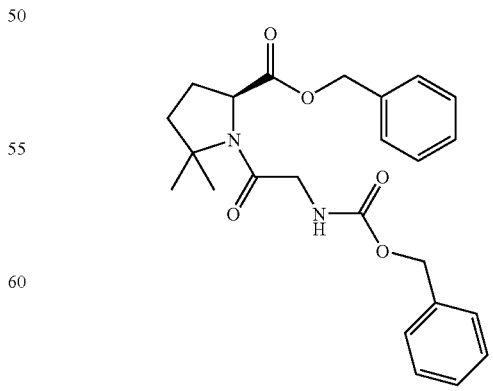

Following general procedure C, 13 was obtained with compound 12 (880 mg, 1.97 mmol, 1.0 eq.), EDCl (450 mg, 2.35 mmol, 1.2 eq.), HOBt (320 mg, 2.37 mmol, 1.2 eq.), Et₃N (0.6 mL, 4.30 mmol, 2.2 eq.) and N-carbobenzyloxyglycine (495 mg, 2.37 mmol, 1.2 eq.). The residue was purified by flash chromatography on silica gel, eluting with cyclohexane-EtOAc (1:0 to 6:4) to afford 13 (535 mg, 64%) as a yellow oil.

Step D: Preparation of 14

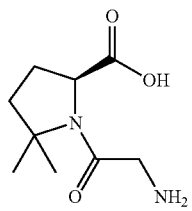

According to general procedure E, 13 (530 mg, 1.25 mmol, 1.0 eq) was deprotected in dichloromethane-methanol (4 mL/1 mL) with palladium on activated carbon 10% (130 mg). The mixture was submitted to hydrogenation at room temperature under 1 atmosphere for 24 hours. The reaction mixture was filtered through Celite® and evaporated to afford 14 (255 mg, quantitative) as a white solid.

Step E: Preparation of 15

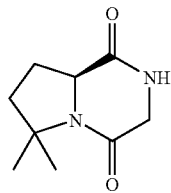

Following general procedure C, 15 was obtained with compound 14 (250 mg, 1.25 mmol, 1.0 eq.), EDCl (290 mg, 1.51 mmol, 1.2 eq.), HOBt (200 mg, 1.48 mmol, 1.2 eq.), Et₃N (0.35 mL, 2.51 mmol, 2.0 eq.) in dichloromethane (5 mL) and DMF (5 mL). The residue was purified by flash chromatography on silica gel, eluting with dichloromethane-methanol (100:0 to 95:5) to afford 15 (150 mg, 66%) as a colorless oil.

Step F: Preparation of 5h

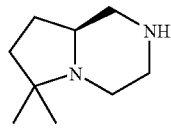

To a suspension of LiAlH₄ (120 mg, 3.16 mmol, 4.0 eq.) in THF (3 mL) at 0° C. was added 15 (140 mg, 0.77 mmol, 1.0 eq.). The reaction mixture was stirred at 70° C. for 1 hour and half. The reaction was cooled to 0° C. and H₂O (0.1 mL), 5N NaOH (0.1 mL) and H₂O (0.1 mL) were added. The resulting mixture was filtered, the precipitate washed with dichloromethane and the filtrate was concentrated under reduced pressure to afford 5h (70 mg, 59%) as a yellow liquid.

Step G: Preparation of 6h

TNOC (50 mg, 0.18 mmol, 1.0 eq.) was coupled with 5h (70 mg, 0.45 mmol, 2.5 eq.) in presence of DABCO (50 mg, 0.45 mmol, 2.5 eq.) and in 0.5 mL of pyridine and 1 ml of acetonitrile. The reaction mixture was stirred at 90° C. for 6 hours and then the mixture was concentrated under reduced pressure and co-evaporated with methanol. The resulting crude product was purified by TLC preparative followed by a trituration in methanol to afford 6h (16 mg, 21%) as a yellow solid.

HPLC (gradient 5% to 95% ACN in H₂O): >95%

MS (ESI⁺) (+0.1% HCOOH): 417.2 [C$_{21}$H$_{25}$FN$_4$O$_4$+H]⁺ (m/z)

mp=220° C.-222° C.

General Scheme for Example XIV:

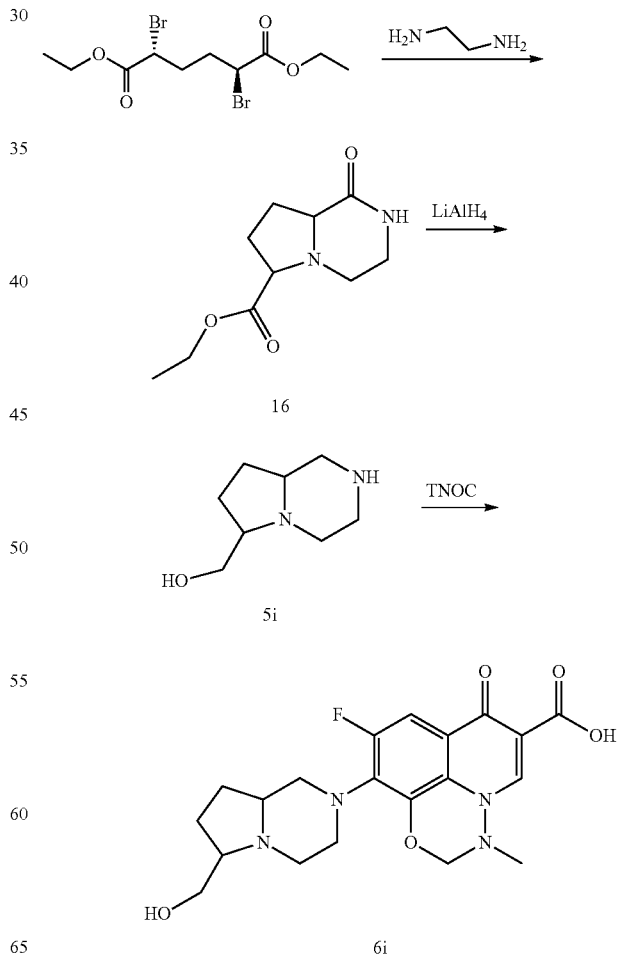

EXAMPLE XIV

8-Fluoro-3-methyl-6-oxo-9-(6-hydroxymethyl-hexahydro-pyrrolo[1,2-a]pyrazin-2-yl)-2,3-dihydro-6H-1-oxa-3,3a-diaza-phenalene-5-carboxylic acid (61)

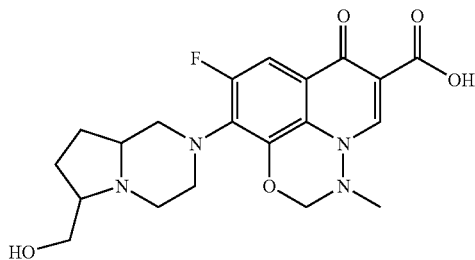

Step A: Preparation of 16

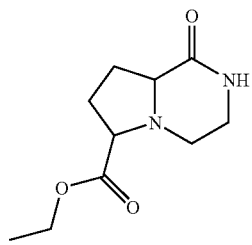

To a solution of 1,2-ethylene diamine (2.0 mL, 29.9 mmol, 2.1 eq.) and $K_2CO_3$ (4.0 g, 28.9 mmol, 2.0 eq.) in $CH_3CN$ (30 mL) at room temperature was added a solution of diethyl meso-2,5-dibromoadipate (5.1 g, 14.2 mmol, 1.0 eq.) in $CH_3CN$ (20 mL) over 2 hours. The reaction mixture was stirred at room temperature for 16 hours. The resulting mixture was filtered, the precipitate washed with dichloromethane and the filtrate was concentrated under reduced pressure. The crude product was purified by flash chromatography on silica gel, eluting with dichloromethane-methanol (100:0 to 90:10) to afford 16 (2.6 g, 86%) as a white solid.

Step B: Preparation of 5i

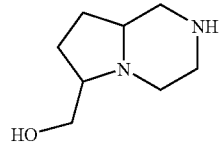

To a suspension of $LiAlH_4$ (1.4 g, 36.9 mmol, 3.0 eq.) in THF (30 mL) at 0° C. was added dropwise a solution of compound 16 (2.6 g, 12.2 mmol, 1.0 eq.) in THF (20 mL) over 45 min. The reaction mixture was stirred at room temperature for 16 hours and then at 80° C. for 2 hours. The reaction was cooled to 0° C. and $H_2O$ (1.6 mL), 10% NaOH (1.6 mL) and $H_2O$ (2.0 mL) were added. The resulting mixture was filtered, the precipitate washed with dichloromethane and the filtrate was concentrated under reduced pressure to afford 51 (1.48 g, 77%) as a colorless oil.

Step C: Preparation of 6i

TNOC (140 mg, 0.50 mmol, 1.0 eq.) was coupled with 51 (230 mg, 1.47 mmol, 2.9 eq.) in presence of DABCO (140 mg, 1.25 mmol, 2.5 eq.) and in 1 mL of pyridine and 2 ml of acetonitrile. The reaction mixture was stirred at 90° C. for 7 hours. The reaction mixture was cooled to room temperature and the precipitate was filtered off and washed with $CH_3CN$ and $Et_2O$ to afford 61 (125 mg, 60%) as a yellow solid.

HPLC (gradient 5% to 95% ACN in $H_2O$): >95%

MS (ESI$^+$) (+0.1% HCOOH): 419.2 $[C_{20}H_{23}FN_4O_5+H]^+$ (m/z)

mp=263° C.-265° C.

General Scheme for Example XV:

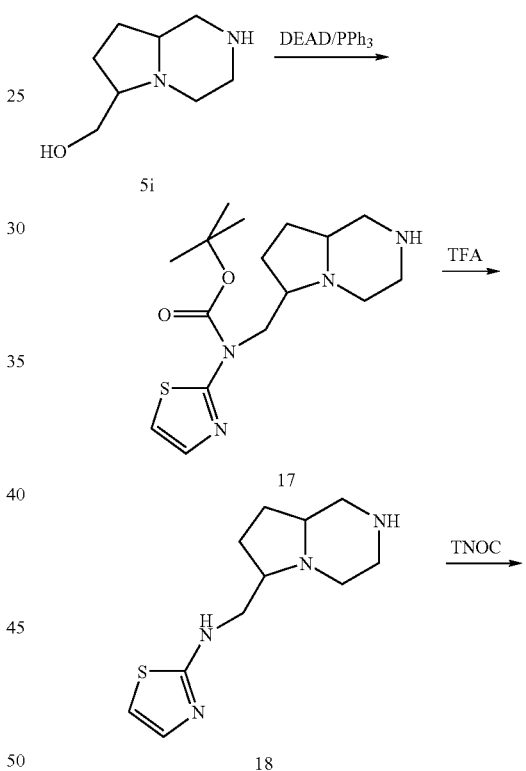

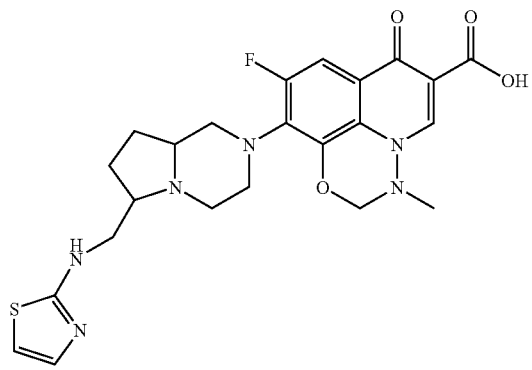

EXAMPLE XV

8-Fluoro-3-methyl-6-oxo-9-[6-(thiazol-2-ylaminomethyl)-hexahydro-pyrrolo[1,2-a]pyrazin-2-yl]-2,3-dihydro-6H-1-oxa-3,3a-diaza-phenalene-5-carboxylic acid (6j)

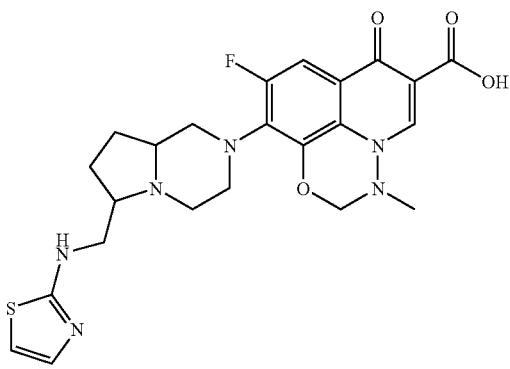

Step A: Preparation of 17

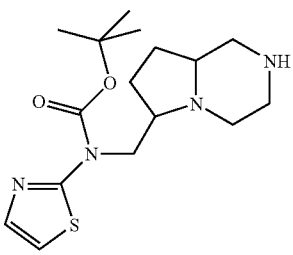

To a suspension of compound 5i (200 mg, 1.28 mmol, 1.0 eq.) in THF (5 mL) at 0° C. were added successively PPh$_3$ (490 mg, 1.87 mmol, 1.5 eq.), DEAD (0.9 mL, 1.96 mmol, 1.5 eq.) and Boc-aminothiazole (310 mg, 1.55 mmol, 1.2 eq.). The reaction mixture was stirred at room temperature for 18 hours. The reaction mixture was concentrated under reduced pressure and the resulting crude product was purified by flash chromatography on silica gel, eluting with dichloromethane-methanol (100:0 to 90:10) to afford 17 (145 mg, 33%) as a yellow oil.

Step B: Preparation of 18

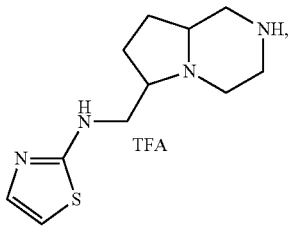

According to general procedure B, 17 (490 mg, 1.44 mmol, 1.0 eq.) was deprotected; the reaction was concentrated under reduced pressure, co-evaporated with methanol and purified on neutral Alumina gel to afford 18 (235 mg, 68%) as a brown oil.

Step C: Preparation of 6j

TNOC (90 mg, 0.32 mmol, 1.0 eq.) was coupled with 5j (230 mg, 0.96 mmol, 3.0 eq.) in presence of DABCO (90 mg, 0.80 mmol, 2.5 eq.) and in 1 mL of pyridine and 2 ml of acetonitrile. The reaction mixture was stirred at 90° C. for 6 hours. The reaction mixture was cooled to room temperature and the crude was concentrated and purified by T.L.C preparative to afford 6j (35 mg, 22%) as a yellow solid.

HPLC (gradient 5% to 95% ACN in H$_2$O): >90%

MS (ESI$^+$) (+0.1% HCOOH): 501.2 [C$_{24}$H$_{27}$FN$_6$O$_4$S+H]$^+$ (m/z)

mp=223° C.-225° C.

General Scheme for the Preparation of Amino Acids (11a, 11b, 11c) Derived from 9-[4-(4-amino-2-fluoro-phenyl)-piperazin-1-yl]-8-fluoro-3-methyl-6-oxo-2,3-dihydro-6H-1-oxa-3,3a-diaza-phenalene-5-carboxylic acid (6)

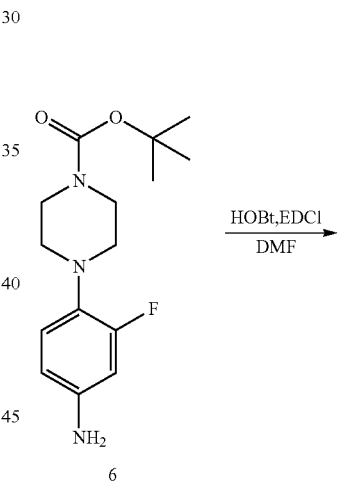

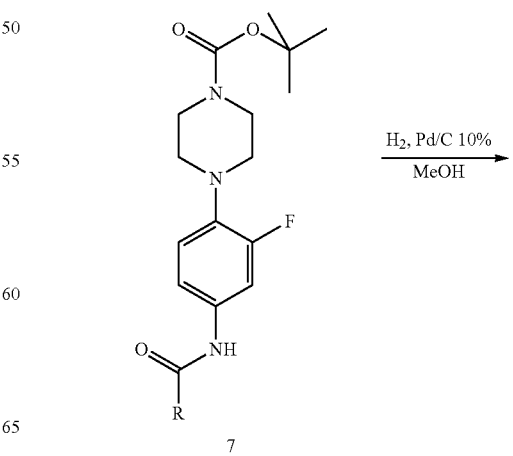

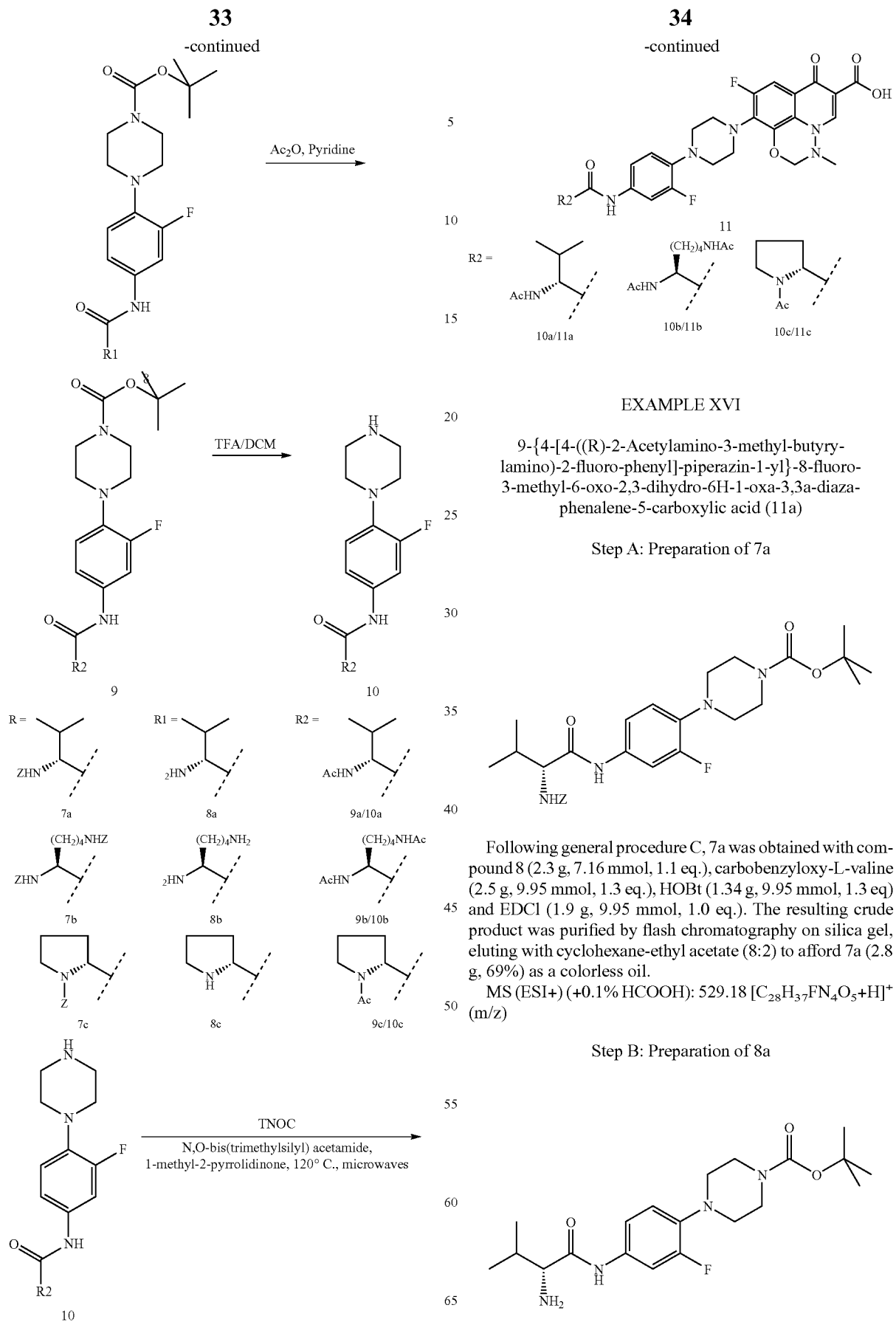

EXAMPLE XVI

9-{4-[4-((R)-2-Acetylamino-3-methyl-butyrylamino)-2-fluoro-phenyl]-piperazin-1-yl}-8-fluoro-3-methyl-6-oxo-2,3-dihydro-6H-1-oxa-3,3a-diaza-phenalene-5-carboxylic acid (11a)

Step A: Preparation of 7a

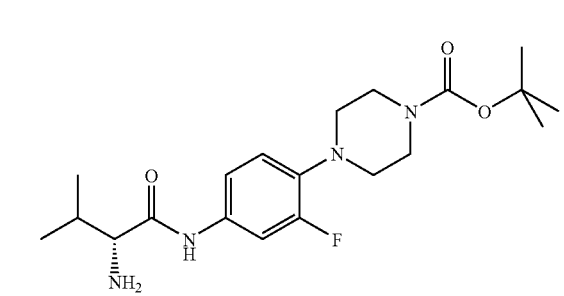

Following general procedure C, 7a was obtained with compound 8 (2.3 g, 7.16 mmol, 1.1 eq.), carbobenzyloxy-L-valine (2.5 g, 9.95 mmol, 1.3 eq.), HOBt (1.34 g, 9.95 mmol, 1.3 eq) and EDCl (1.9 g, 9.95 mmol, 1.0 eq.). The resulting crude product was purified by flash chromatography on silica gel, eluting with cyclohexane-ethyl acetate (8:2) to afford 7a (2.8 g, 69%) as a colorless oil.

MS (ESI+) (+0.1% HCOOH): 529.18 $[C_{28}H_{37}FN_4O_5+H]^+$ (m/z)

Step B: Preparation of 8a

To a solution of 7a (1.30 g, 2.46 mmol) in methanol (60 mL) was added Pd/C (121 mg). The reaction mixture was submitted to hydrogenation at atmospheric pressure and at room temperature for 18 hours. The reaction was filtered over Celite® and evaporated under reduced pressure. The residue was used as crude without further purification (940 mg).

Step C: Preparation of 9a

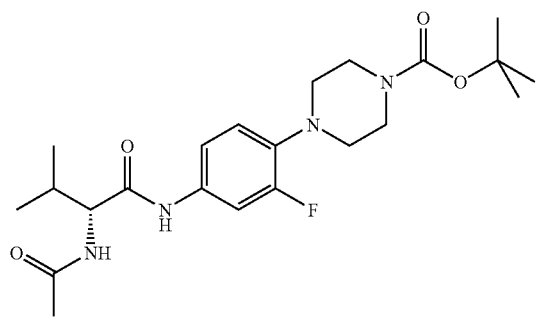

To a solution of 8a (940 mg, 2.38 mmol, 1.0 eq.) in DCM (30 mL) cooled to 0° C. were added pyridine (0.3 mL, 2.86 mmol, 1.2 eq.) and trifluoroacetic anhydride (0.8 mL, 8.34 mmol, 3.5 eq.). The reaction mixture was stirred at room temperature for 2 hours. The reaction mixture was concentrated under reduced pressure. The resulting crude product was purified by flash chromatography on silica gel, eluting with cyclohexane-ethyl acetate (5:5 to 0:1) to afford 9a (950 mg, 91%) as a colorless oil.

Step D: Preparation of 10a

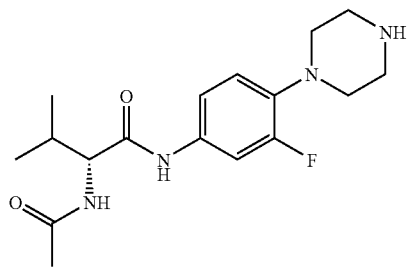

Following general procedure B, 9a (950 mg, 2.18 mmol) was deprotected. The residue was purified by flash chromatography on silica gel, eluting with dichloromethane-methanol (95:5 to 90:10) then dichloromethane—10% 7N NH$_3$ in methanol to afford 10a (210 mg, 96%).

MS (ESI+) (+0.1% HCOOH): 337.08 [C$_{17}$H$_{25}$FN$_4$O$_2$+H]$^+$ (m/z)

Step E: Preparation of 11a

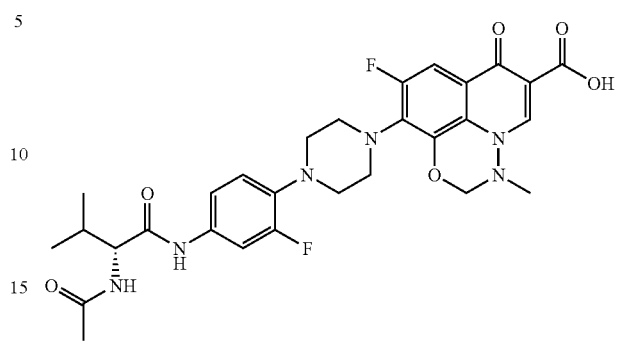

Following general procedure D, TNOC (188 mg, 0.67 mmol, 1.0 eq.) was coupled with 10a (449 mg, 1.33 mmol, 2.0 eq.) in 1-methyl-2-pyrrolidinone (5 mL) with N,O-bis(trimethylsilyl)acetamide (163 µL, 0.67 mmol, 1.0 eq.) and N-methylmorpholine (161 µL, 1.47 mmol, 2.2 eq.). The mixture was submitted to microwaves for 1 hour at 120° C. The reaction was cooled to 0° C. and H$_2$O was added, the precipitate was filtered and washed with H$_2$O. The solid was triturated with hot methanol and filtrated to afford the title compound (95 mg, 24%).

HPLC (gradient 5%-80% ACN in H$_2$O): >99%

MS (ESI+) (+0.1% HCOOH): 599.30 [C$_{29}$H$_{32}$FN$_6$O$_6$+H]$^+$ (m/z)

mp=262° C.-264° C.

EXAMPLE XVII

9-{4-[4-((R)-Z 6-Bis-acetylamino-hexanoylamino)-2-fluoro-phenyl]-piperazin-1-yl}-8-fluoro-3-methyl-6-oxo-2,3-dihydro-6H-1-oxa-3,3a-diaza-phenalene-5-carboxylic acid (1b)

Step A: Preparation of 7b

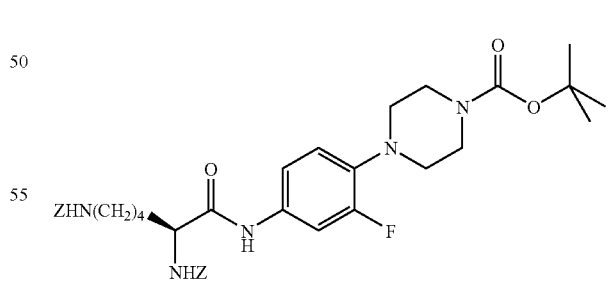

Following general procedure C, 7b was obtained with compound 6 (1.5 g, 5.07 mmol, 1.0 eq.), EDCl (1.2 g, 6.1 mmol, 1.2 eq.), HOBt (823 mg, 6.1 mmol, 1.2 eq.) and N,N-carbobenzyloxy-Lysine (2.5 g, 6.1 mmol, 1.2 eq.). The residue was purified by flash chromatography on silica gel, eluting with cyclohexane-ethyl acetate (8:2 to 5:5) to afford 7b (2.9 g, 82%) as a beige foam.

MS (ESI+) (+0.1% HCOOH): 328.12 [C18H$_{21}$N$_3$O$_3$+H]$^+$ (m/z)

Step B: Preparation of 8b

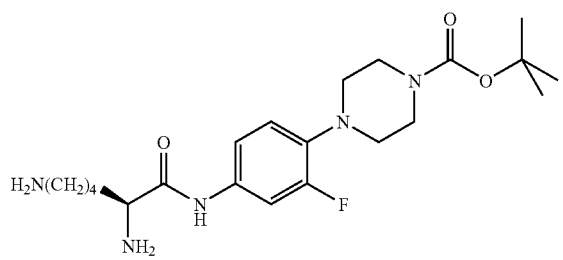

As described for compound 8a, 8b was obtained starting from 7b (1.63 g, 2.35 mmol) using Pd/C (1.0 g). The residue was used as crude without further purification (1.5 g).

Step C: Preparation of 9b

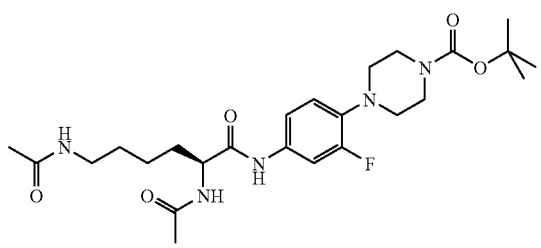

As described for compound 9a, 9b was obtained starting from 8b (1.5 g, 3.0 mmol), pyridine (5 mL, 47.6 mmol) and trifluoroacetic anhydride (4 mL, 41.7 mmol). The residue was purified by flash chromatography on silica gel, eluting with dichloromethane-methanol (95:5 to 90:10) to afford 9b (995 mg, 83%) as a white powder.

Step D: Preparation of 10b

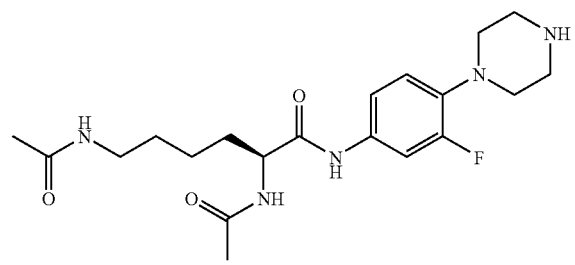

Following general procedure B, 9b (995 mg, 1.96 mmol) was deprotected. The residue was purified by flash chromatography on silica gel, eluting with dichloromethane-methanol (95:5 to 90:10) then dichloromethane—10% 7N NH$_3$ in methanol to afford 10b (798 mg, 100%).

MS (ESI+) (+0.1% HCOOH): 408.16 [C$_{20}$H$_{30}$FN$_5$O$_3$+H]$^+$ (m/z)

Step E: Preparation of 11 b

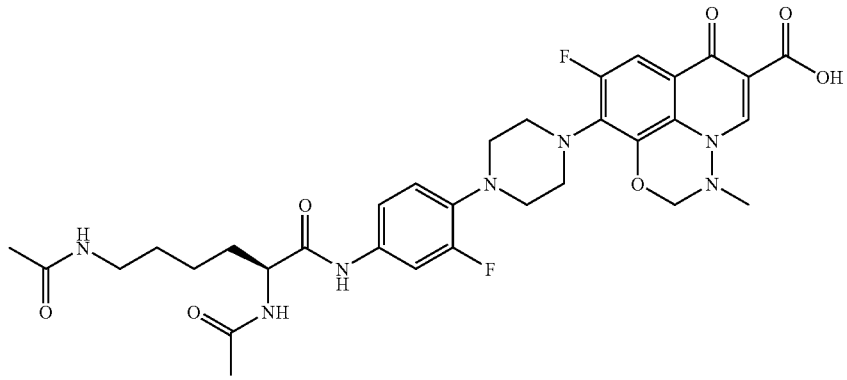

Following general procedure D, TNOC (140 mg, 0.50 mmol, 1.0 eq.) was coupled with 10b (406 mg, 0.99 mmol, 2.0 eq.) in 1-methyl-2-pyrrolidinone (2 mL) with N,O-bis(trimethylsilyl)acetamide (122 µL, 0.5 mmol, 1.0 eq.) and N-methylmorpholine (250 µL, 1.0 mmol, 2.2 eq). The mixture was submitted to microwaves for 30 min twice at 120° C. The reaction was cooled to 0° C. and H$_2$O was added, the precipitate was filtered and washed with H$_2$O. The solid was triturated with hot methanol and filtrated to afford the title compound (160 mg, 24%).

HPLC (gradient 5%-80% ACN in H$_2$O): >99%

MS (ESI+) (+0.1% HCOOH): 621.30 [C$_{32}$H$_{37}$F$_2$N$_7$O$_7$+H]$^+$ (m/z)

mp=225° C.-276° C.

EXAMPLE XVIII 9-(4-{4-[(1-Acetyl-pyrrolidine-2-carbonyl)-amino]-2-fluoro-phenyl}-piperazin-1-yl)-8-fluoro-3-methyl-6-oxo-2,3-dihydro-6H-1-oxa-3,3a-diaza-phenalene-5-carboxylic acid (11c)

Step A: Preparation of 7c

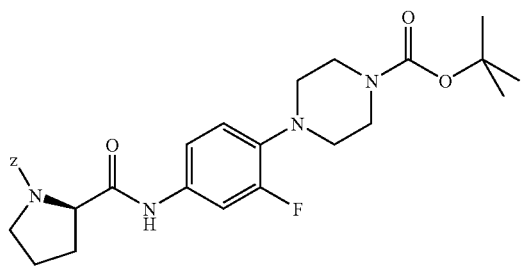

Following general procedure C, 7c was obtained with compound 6 (1.9 g, 6.69 mmol, 1.0 eq.), EDCl (1.9 g, 10.0 mmol, 1.5 eq.), HOBt (1.36 g, 10.0 mmol, 1.5 eq.) and N-carbobenzyloxylproline (2.5 g, 10.0 mmol, 1.5 eq.). The residue was purified by flash chromatography on silica gel, eluting with cyclohexane-ethyl acetate (8:2 to 5:5) to afford 7c (3.5 g, 99%).

MS (ESI+) (+0.1% HCOOH): 527.14 $[C_{28}H_{35}FN_4O_5+H]^+$ (m/z)

Step B: Preparation of 8c

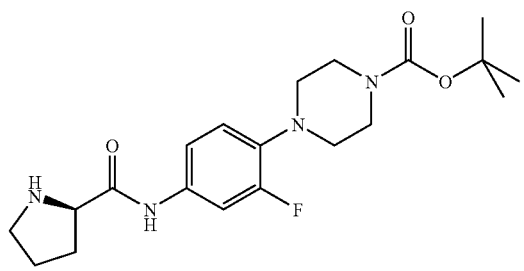

As described for compound 8a, 8c was obtained starting from 7c (3.5 g, 6.16 mmol) using Pd/C (0.5 g). The residue was used as crude without further purification (2.6 g).

Step C: Preparation of 9c

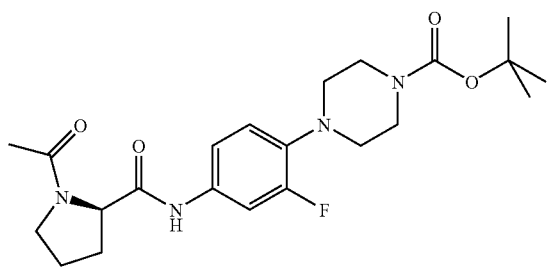

As described for compound 9a, 9c was obtained starting from 8c (2.5 g, 6.16 mmol, 1.0 eq.), pyridine (1.1 mL, 13.3 mmol, 2.0 eq.) and trifluoroacetic anhydride (2.5 mL, 26.6 mmol, 4.0 eq.). The residue was purified by flash chromatography on silica gel, eluting with dichloromethane-methanol (98:2) to afford 9c (2.6 g, 90%).

Step D: Preparation of 10c

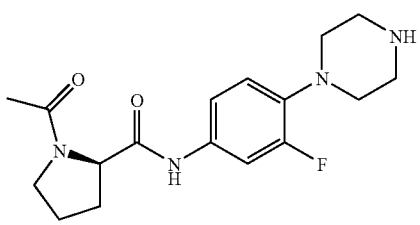

Following general procedure B, 9c (2.6 g, 6.0 mmol) was deprotected. The residue was purified by flash chromatography on silica gel, eluting with dichloromethane—7N $NH_3$ in methanol (95:5) to afford 10c (1.7 g, 85%).

Step E: Preparation of 11c

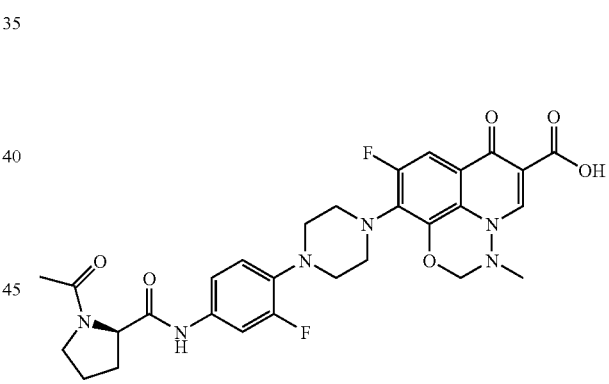

Following general procedure D, TNOC (337 mg, 1.2 mmol, 1.0 eq.) was coupled with 10c (800 mg, 2.39 mmol, 2.0 eq.) in 1-methyl-2-pyrrolidinone (8 mL) with N,O-bis(trimethylsilyl)acetamide (293 µL, 1.2 mmol, 1.0 eq.) and N-methylmorpholine (289 µL, 2.63 mmol, 2.2 eq.). The mixture was submitted to microwaves for 1 hour at 120° C. The reaction was cooled to 0° C. and $H_2O$ was added, the precipitate was filtered and washed with $H_2O$. The solid was triturated with hot methanol and filtrated to afford the title compound (100 mg, 14%) as a white solid.

HPLC (gradient 5%-80% ACN in $H_2O$): >95%

MS (ESI+) (+0.1% HCOOH): 597.30 $[C_{29}H_{30}F_2N_6O_6+H]^+$ (m/z)

mp=199° C.-201° C.

General Scheme for the Preparation of (14a, 14b, 14c) Derived from 9-[4-(4-amino-2-fluoro-phenyl)-piperazin-1-yl]-8-fluoro-3-methyl-6-oxo-Z 3-dihydro-6H-1-oxa-3,3a-diaza-phenalene-5-carboxylic acid

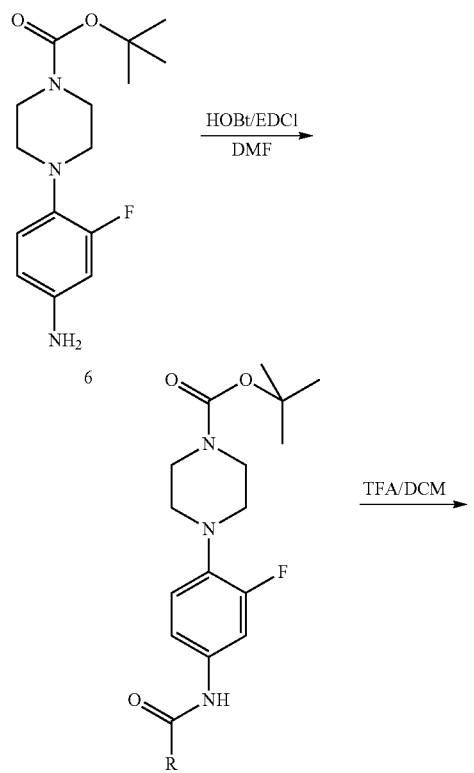

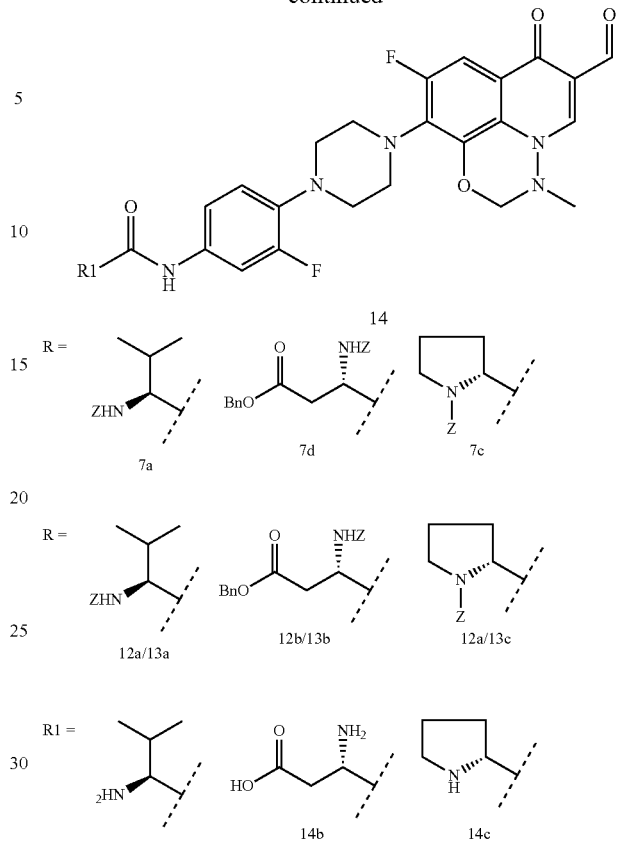

EXAMPLE XIX

9-{4-[4-(2-Amino-3-methyl-butyrylamino)-2-fluoro-phenyl]-piperazin-1-yl}-8-fluoro-3-methyl-6-oxo-2,3-dihydro-6H-1-oxa-3,3a-diaza-phenalene-5-carboxylic acid (14a)

Step A: Preparation of 12a

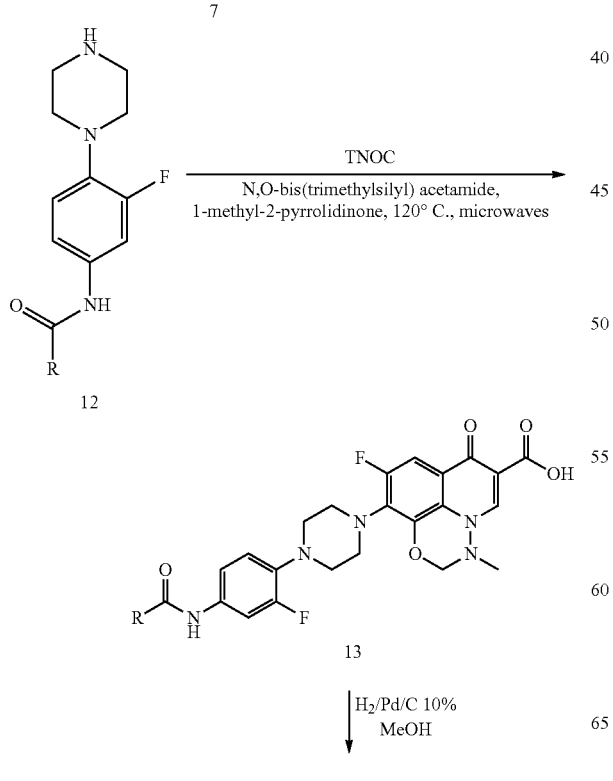

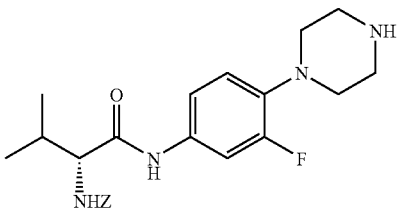

Following general procedure B, 7a (1.3 g, 2.46 mmol) was deprotected. The residue was purified by flash chromatography on silica gel, eluting with dichloromethane—7N NH$_3$ in methanol (95:5) to afford 12a (1.0 g, 97%).

MS (ESI+) (+0.1% HCOOH): 429.03 [C$_{23}$H$_{29}$FN$_4$O$_3$+H]$^+$ (m/z)

Step B: Preparation of 13a

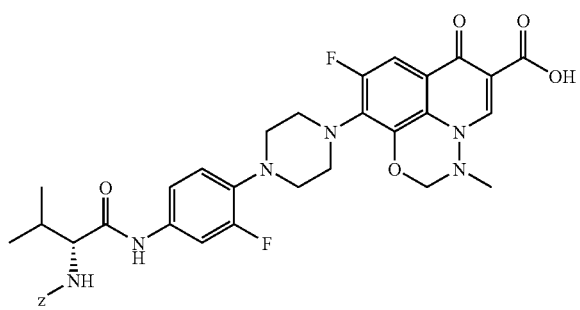

Following general procedure D, TNOC (224 mg, 0.97 mmol, 1.0 eq.) was coupled with 12a (830 mg, 1.94 mmol, 2.0 eq.) in 1-methyl-2-pyrrolidinone (8 mL) with N,O-bis(trimethylsilyl)acetamide (237 µL, 0.96 mmol, 1.0 eq.) and N-methylmorpholine (234 µL, 2.13 mmol, 2.2 eq.). The mixture was submitted to microwaves for 30 min twice at 120° C. The reaction was cooled to 0° C. and H$_2$O was added, the precipitate was filtered and washed with H$_2$O. The solid was triturated with hot methanol and filtrated to afford the title compound (200 mg, 30%) as a white solid.

HPLC (gradient 5%-80% ACN in H$_2$O): >99%

MS (ESI+) (+0.1% HCOOH): 691.43 [C$_{35}$H$_{36}$F$_2$N$_6$O$_7$+H]$^+$ (m/z)

Step C: Preparation of 14a

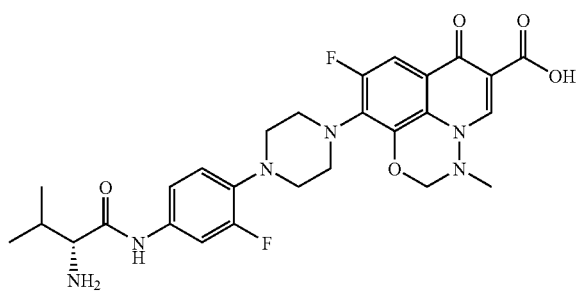

As described for compound 8a, 14a was obtained starting from 13a (200 mg, 0.29 mmol) using Pd/C (20 mg). The residue was triturated in DCM to afford the title compound (112.5 mg, 21%).

HPLC (gradient 5%-80% ACN in H$_2$O): >99%

MS (ESI+) (+0.1% HCOOH): 557.20 [C$_{27}$H$_{30}$F$_2$N$_6$O$_5$+H]$^+$ (m/z)

mp=dec.

EXAMPLE XX

9-{4-[4-(2-Amino-3-carboxy-propionylamino)-2-fluoro-phenyl]-piperazin-1-yl}-8-fluoro-3-methyl-6-oxo-2,3-dihydro-6H-1-oxa-3,3a-diaza-phenalene-5-carboxylic acid

Step A: Preparation of 7d

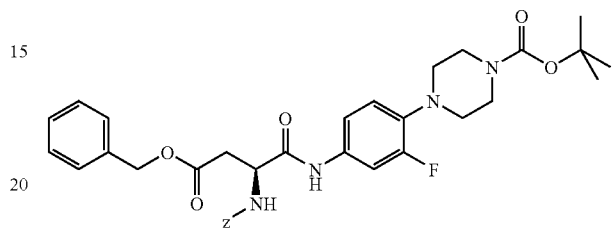

Following general procedure C, 7d was obtained with compound 6 (1.3 g, 4.48 mmol, 1.0 eq.), EDCl (1.3 g, 6.23 mmol, 1.5 eq.), HOBt (0.9 g, 6.23 mmol, 1.5 eq.) and N-carbobenzyloxylasparaginebenzylcarboxylic acid (2.4 g, 6.23 mmol, 1.5 eq.). The residue was purified by flash chromatography on silica gel, eluting with cyclohexane-ethyl acetate (8:2 to 5:5) to afford 7d (2.5 g, 87%).

Step B: Preparation of 12b

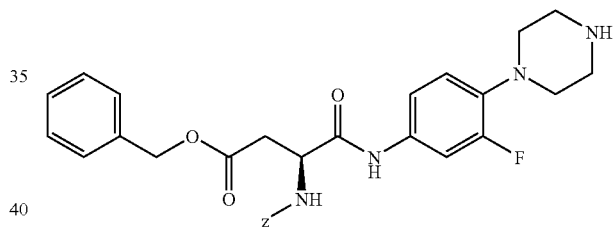

Following general procedure B, 7d (2.5 g, 2.46 mmol) was deprotected. The residue was purified by flash chromatography on silica gel, eluting with dichloromethane—7N NH$_3$ in methanol (95:5) to afford 12b (1.8 g, 85%).

Step C: Preparation of 13b

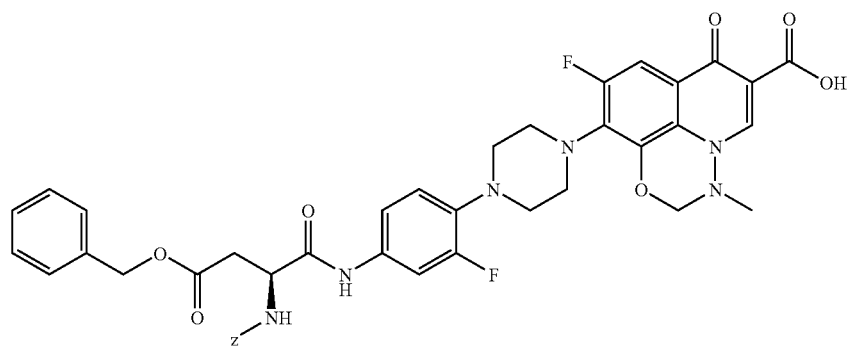

Following general procedure D, TNOC (211 mg, 0.75 mmol, 1.0 eq.) was coupled with 12b (800 mg, 1.50 mmol, 2.0 eq.) in 1-methyl-2-pyrrolidinone (8 mL) with N,O-bis(trimethylsilyl)acetamide (184 µL, 0.75 mmol, 1.0 eq.) and N-methylmorpholine (182 µL, 1.16 mmol, 2.2 eq.). The mixture was submitted to microwaves for 30 min twice at 120° C. The reaction was cooled to 0° C. and H₂O was added, the precipitate was filtered and washed with H₂O. The solid was purified by T.L.C preparative to afford the title compound (120 mg, 10%) as a white solid.

HPLC (gradient 5%-80% ACN in H₂O): >95%

MS (ESI+) (+0.1% HCOOH): 592.08 [$C_{30}H_{27}F_2N_5O_6$+H]⁺ (m/z)

Step D: Preparation of 14b

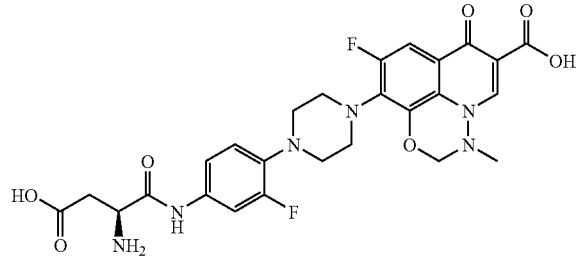

As described for compound 8a, 14b was obtained starting from 13b (120 mg, mmol) using Pd/C (20 mg). The residue was triturated in Et₂O, filtrated, washed with MeOH and DCM to afford the title compound (50 mg, 56%).

HPLC (gradient 5%-80% ACN in H₂O): >95%

MS (ESI+) (+0.1% HCOOH): 524.20 [$C_{26}H_{26}F_2N_6O_7$+H]⁺ (m/z)

mp=218° C. dec.

EXAMPLE XXI

8-Fluoro-9-(4-{2-fluoro-4-[(pyrrolidine-2-carbonyl)-amino]-phenyl}-piperazin-1-yl)-3-methyl-6-oxo-2,3-dihydro-6H-1-oxa-3,3a-diaza-phenalene-5-carboxylic acid (14c)

Step A: Preparation of 12c

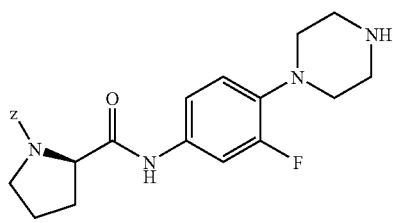

Following general procedure B, 7c (1.5 g, 2.85 mmol) was deprotected. The residue was purified by flash chromatography on silica gel, eluting with dichloromethane—7N NH₃ in methanol (98:2 to 95:5) to afford 12c (1.2 g, 99%).

MS (ESI+) (+0.1% HCOOH): 427.10 [$C_{23}H_{27}FN_4O_3$+H]⁺ (m/z)

Step B: Preparation of 13c

Following general procedure D, TNOC (285 mg, 1.0 mmol, 1.0 eq.) was coupled with 12c (860 mg, 2.0 mmol, 2.0 eq.) in 1-methyl-2-pyrrolidinone (8 mL) with N,O-bis(trimethylsilyl)acetamide (246 µL, 1.0 mmol, 1.0 eq.) and N-methylmorpholine (244 µL, 2.22 mmol, 2.2 eq.). The mixture was submitted to microwaves for 1 hour at 120° C. The reaction was cooled to 0° C. and H₂O was added, the precipitate was filtered and washed with H₂O. The solid was triturated with hot methanol and filtrated to afford the title compound (120 mg, 17%).

HPLC (gradient 5%-80% ACN in H₂O): >99%

MS (ESI+) (+0.1% HCOOH): 689.19 [$C_{35}H_{34}F_2N_6O_7$+H]⁺ (m/z)

Step C: Preparation of 14c

As described for compound 8a, 14c was obtained starting from 13c (120 mg, 0.34 mmol) using Pd/C (20 mg). The residue was triturated in DCM to afford the title compound (76 mg, 79%) as a beige solid.

HPLC (gradient 5%-80% ACN in H₂O): >95%

MS (ESI+) (+0.1% HCOOH): 555.30 [$C_{27}H_{28}F_2N_6O_5$+H]⁺ (m/z)

mp=dec.

General Scheme for the Preparation of Pyridazinone Piperazines Derivatives

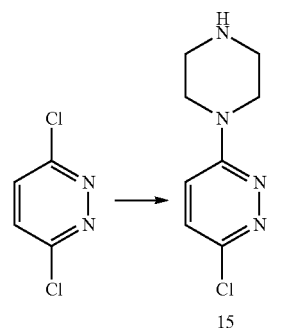

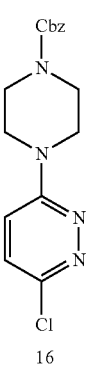

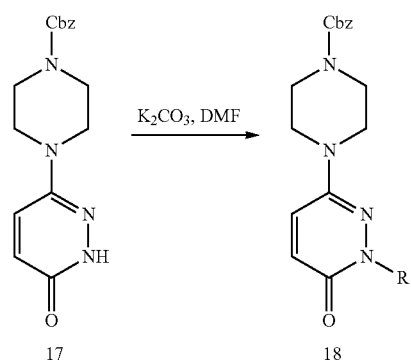

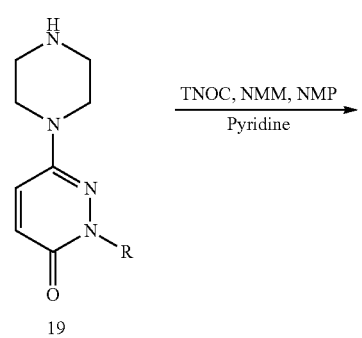

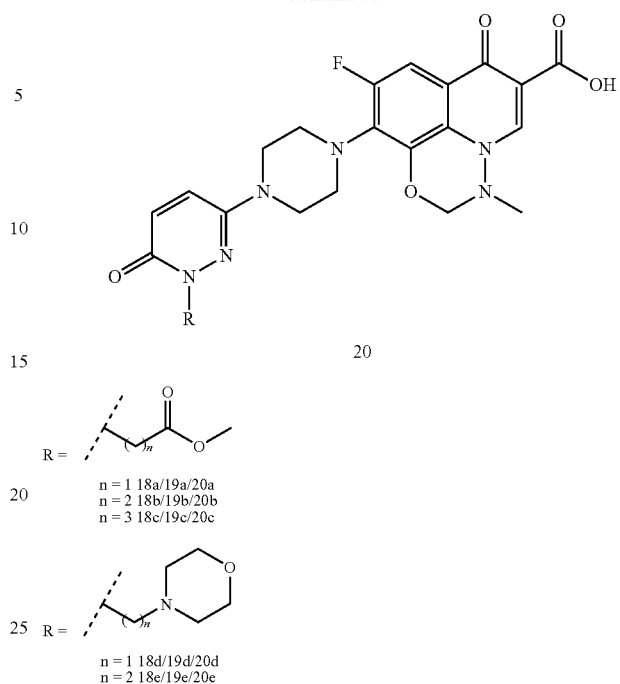

EXAMPLE XXII

8-Fluoro-9-[4-(1-methoxycarbonylmethyl-6-oxo-1,6-dihydro-pyridazin-3-yl)-piperazin-1-yl]-3-methyl-6-oxo-2,3-dihydro-6H-1-oxa-3,3a-diaza-phenalene-5-carboxylic acid (20a)

Step A: Preparation of 15

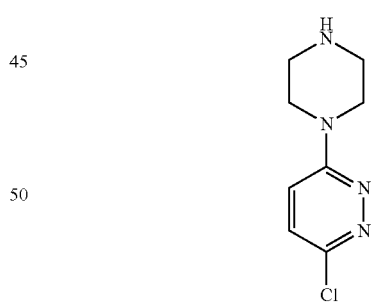

To a solution of dichloropyridazine (10.0 g, 67.1 mmol, 1.0 eq.) and piperazine (25 g, 268 mmol, 4 eq.) in EtOH (200 mL) was added DIEPA (11.7 mL, 67.1 mmol, 1.0 eq.). The reaction mixture was stirred at reflux for 18 hours. The reaction mixture was concentrated under reduced pressure. The residue was diluted with CHCl₃ and the organic phase was washed with H₂O. The organic extracts were dried over MgSO₄ and concentrated. The resulting crude product was purified by flash chromatography on silica gel, eluting with dichloromethane-methanol-ammoniac (93:5:2 to 88:10:2) to afford 15 (11.1 g, 82%) as a light yellow solid.

MS (ESI+) (+0.1% HCOOH): 198.89 $[C_8H_{11}N_4{}^+H]^+$ (m/z)

Step B: Preparation of 16

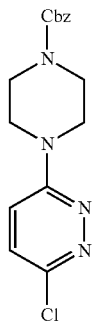

To a suspension of 15 (1.1 g, 5.54 mmol, 1.0 eq.) in acetone (10 mL) and H$_2$O (10 mL) cooled to 0° C., were added Na$_2$CO$_3$ (880 mg, 8.3 mmol, 1.5 eq.) and benzylchloroformate (1.2 mL, 8.3 mmol, 1.5 eq.). The reaction mixture was stirred at room temperature for 18 hours. The reaction mixture was filtrated, the filtrate was washed with H$_2$O and dried. The crude product was purified by flash chromatography on silica gel, eluting with dichloromethane-methanol (95:5 to 90:10) to afford 16 (1.49 g, 81%) as a white solid.

MS (ESI+) (+0.1% HCOOH): 333.08 $[C_{16}H_{17}ClN_4O_2+H]^+$ (m/z)

Step C: Preparation of 17

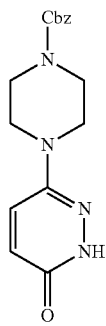

To a solution of 16 (1.0 g, 3.0 mmol, 1.0 eq.) in AcOH (75 mL) was added sodium acetate (252 mg, 9.0 mmol, 3.0 eq.). The reaction mixture was stirred at 120° C. for 18 hours. The reaction mixture was co-evaporated with toluene. The residue was diluted with EtOAc, the organic phase was washed with a saturated aqueous solution of NaHCO$_3$. The organic extracts were dried over MgSO$_4$ and concentrated. The crude product was purified by flash chromatography on silica gel, eluting with dichloromethane-methanol (98:2 to 95:5) to afford 17 (780 mg, 82%) as a yellow solid.

General Procedure F for Pyridazinone 17 Alkylation Reactions

To a solution of compound 17 in DMF was added K$_2$CO$_3$ and then the halide derivate. The mixture was stirred at 16° C. between 6 hours and 18 hours. The reaction mixture was diluted with EtOAC and the organic phase was washed with a saturated aqueous solution of NH$_4$Cl. The organic extracts were dried over MgSO$_4$ and concentrated.

Step D: Preparation of 18a

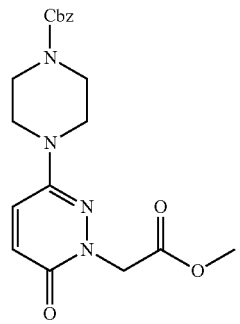

Following general procedure F, 18a was obtained starting from compound 17 (780 mg, 2.5 mmol, 1.0 eq.) and methylbromoacetate (215 µL, 7.5 mmol, 3.0 eq.) and K$_2$CO$_3$ (857 mg, 6.25 mmol, 2.5 eq.). The crude product was purified by flash chromatography on silica gel, eluting with cyclohexane-ethyl acetate (5:5 to 0:1) to afford 18a (900 mg, 94%) as a yellow solid.

Step E: Preparation of 19a

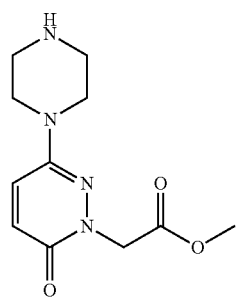

As described for compound 8a, 19a was obtained starting from 18a (900 mg, 2.5 mmol) using Pd/C (80 mg). The crude was purified by flash chromatography on silica gel, eluting with dichloromethane—7N NH$_3$ in methanol (95:5 to 90:10) to afford 19a (510 mg, 85%).

Step F: Preparation of 20a

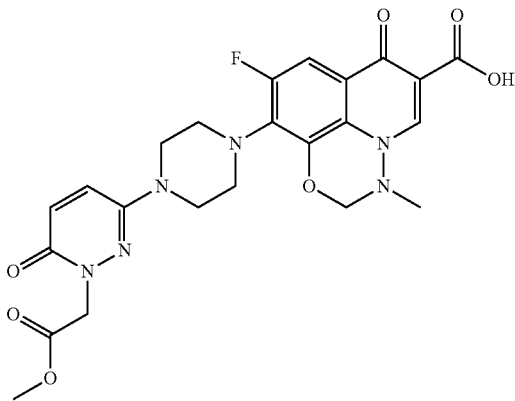

To a solution of 19a (510 mg, 2.0 mmol, 2.0 eq.) in pyridine (2.5 mL) and N-methylpyrrolidinone (0.5 mL) were added N-methylmorpholine (0.4 mL, 8.0 mmol, 4.0 eq.) and TNOC (285 mg, 1.0 mmol, 1.0 eq.). The reaction mixture was stirred in a sealed tube at 120° C. for 18 hours. The reaction was cooled to 0° C. and co-evaporated with toluene and methanol. The residue was triturated with hot methanol and filtrated to afford the title compound (145 mg, 26%) as a beige solid.

HPLC (gradient 5%-80% ACN in H$_2$O): >90%

MS (ESI+) (+0.1% HCOOH): 515.17 [C$_{35}$H$_{23}$F$_2$N$_6$O$_7$+H]$^+$ (m/z)

mp=305° C.-307° C.

EXAMPLE XXIII

8-Fluoro-9-{4-[1-(2-methoxycarbonyl-ethyl)-6-oxo-1,6-dihydro-pyridazin-3-yl]-piperazin-1-yl}-3-methyl-6-oxo-2,3-dihydro-6H-1-oxa-3,3a-diaza-phenalene-5-carboxylic acid (20b)

Step A: Preparation of 18b

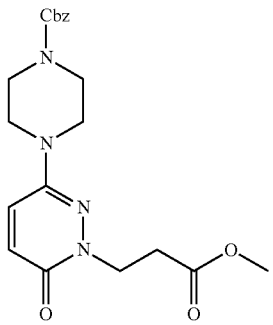

Following general procedure F, 18b was obtained starting from compound 17 (1.30 g, 4.13 mmol, 1.0 eq.) and methyl-bromopropionate (1.4 mL, 3.9 mmol, 3.0 eq.) and K$_2$CO$_3$ (1.40 g, 10.3 mmol, 2.5 eq.). The crude product was purified by flash chromatography on silica gel, eluting with cyclohexane-ethyl acetate (5:5 to 0:1) to afford 18b (1.6 g, 97%) as a yellow gum.

Step B: Preparation of 19b

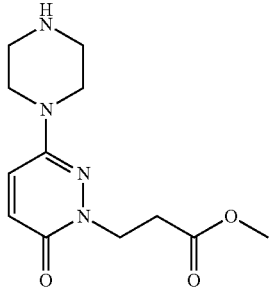

As described for compound 8a, 19b was obtained starting from 18b (1.6 g, 4.0 mmol) using Pd/C (200 mg). The crude was purified by flash chromatography on silica gel, eluting with dichloromethane—7N NH$_3$ in methanol (95:5 to 90:10) to afford 19b (1.0 g, 94%).

Step C: Preparation of 20b

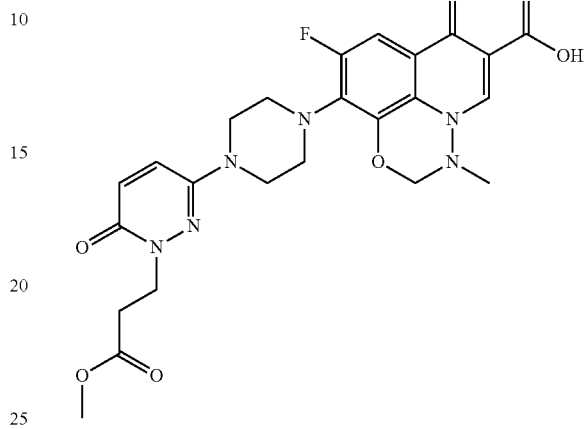

As described for compound 20a, 20b was obtained starting from 19b (1.0 g, 3.75 mmol, 2.0 eq.), pyridine (5 mL), N-methylmorpholine (1.0 mL, 20.0 mmol, 4.0 eq.) and TNOC (535 mg, 1.87 mmol, 1.0 eq.). 57 mg of the crude were purified by T.L.C. preparative to afford the title compound (25 mg, 23%) as a yellow solid.

HPLC (gradient 5%-80% ACN in H$_2$O): >90%

MS (ESI+) (+0.1% HCOOH): 529.10 [C$_{24}$H$_{25}$F$_2$N$_6$O$_7$+H]$^+$ (m/z)

mp=262° C. dec.

EXAMPLE XXIV

8-Fluoro-9-{4-[1-(3-methoxycarbonyl-propyl)-6-oxo-1,6-dihydro-pyridazin-3-yl]-piperazin-1-yl}-3-methyl-6-oxo-2,3-dihydro-6H-1-oxa-3,3a-diaza-phenalene-5-carboxylic acid (20c)

Step A: Preparation of 18c

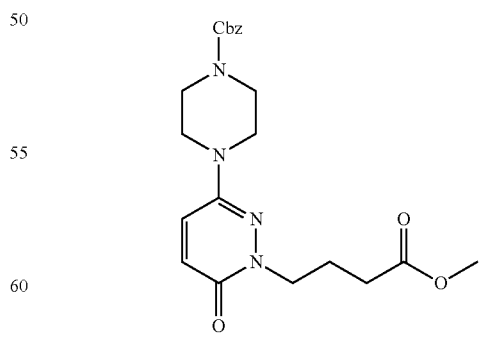

Following general procedure F, 18c was obtained starting from compound 17 (1.25 g, 3.97 mmol, 1.0 eq.), methyl-4-bromobutyrate (2.2 g, 12.15 mmol, 3.0 eq.) and K$_2$CO$_3$ (1.4 g, 10.3 mmol, 2.5 eq.). The crude product was purified by flash chromatography on silica gel, eluting with cyclohexane-ethyl acetate (5:5 to 0:1) to afford 18c (1.52 g, 92%) as a yellow gum.

MS (ESI+) (+0.1% HCOOH): 415.10 [C$_{21}$H$_{26}$N$_4$O$_5$+H]$^+$ (m/z)

Step B: Preparation of 19c

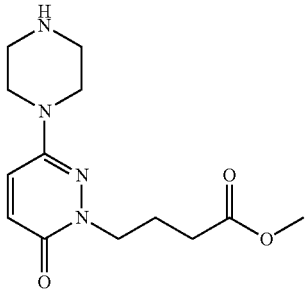

As described for compound 8a, 19c was obtained starting from 18c (1.5 g, 3.61 mmol) using Pd/C (150 mg). The crude product was purified by flash chromatography on silica gel, eluting with dichloromethane—7N NH$_3$ in methanol (95:5 to 90:10) to afford 19c (953 mg, 94%).

MS (ESI+) (+0.1% HCOOH): 249.02 [C$_{13}$H$_{20}$N$_4$O$_3$+H]$^+$ (m/z)

Step C: Preparation of 20c

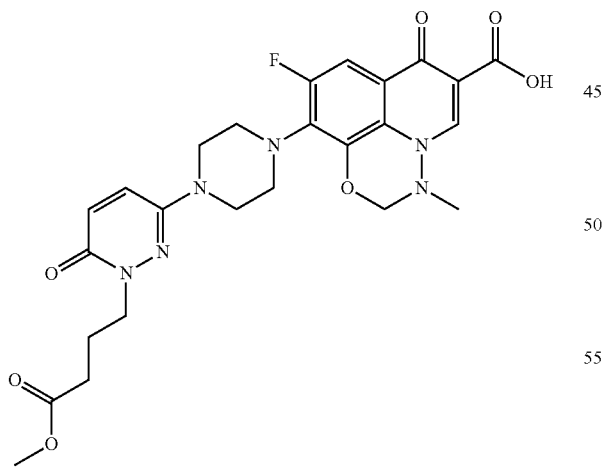

As described for compound 20a, 20c was obtained starting from 19c (953 mg, mmol, 2.0 eq.) in pyridine (5 mL) and N-methylmorpholine (1.0 mL, 20.0 mmol, 4.0 eq.) and TNOC (480 mg, 1.7 mmol, 1.0 eq.). The crude product was purified by T.L.C. preparative to afford the title compound (35 mg, 4%) as a yellow solid.

HPLC (gradient 5%-80% ACN in H$_2$O): >90%

MS (ESI+) (+0.1% HCOOH): 543.10 [C$_{25}$H$_{27}$FN$_6$O$_7$+H]$^+$ (m/z)

mp=192° C.-194° C.

EXAMPLE XXV

8-Fluoro-3-methyl-9-{4-[1-(2-morpholin-4-yl-2-oxo-ethyl)-6-oxo-1,6-dihydro-pyridazin-3-yl]-piperazin-1-yl}-6-oxo-2,3-dihydro-6H-1-oxa-3,3a-diazaphenalene-5-carboxylic acid (20d)

Step A: Preparation of 18d

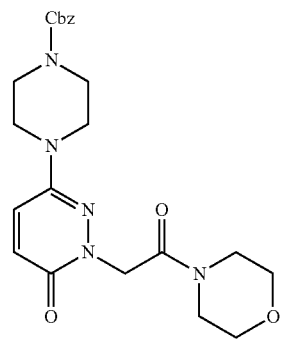

Following general procedure F, 18d was obtained starting from compound 17 (1.0 g, 3.18 mmol, 1.0 eq.), 2-chloro-1-morpholinoethan-1-one (1.04 g, 6.40 mmol, 2.0 eq.) and K$_2$CO$_3$ (1.10 g, 7.95 mmol, 2.5 eq.). The crude product was purified by flash chromatography on silica gel, eluting with dichloromethane-methanol (99:1 to 90:10) to afford 18d (1.25 g, 89%) as a yellow foam.

Step B: Preparation of 19d

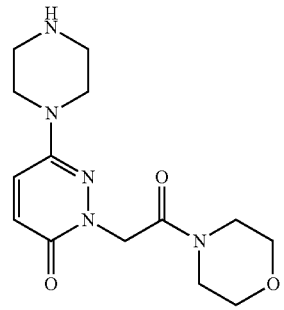

As described for compound 8a, 19d was obtained starting from 18d (1.25 g, 2.83 mmol) using Pd/C (200 mg). The crude product was purified by flash chromatography on silica gel, eluting with dichloromethane—7N NH$_3$ in methanol (95:5 to 90:10) to afford 19d (877 mg, 100%).

MS (ESI+) (+0.1% HCOOH): 308.18 [C$_{14}$H$_2$, N$_5$O$_3$+H]$^+$ (m/z)

Step C: Preparation of 20d

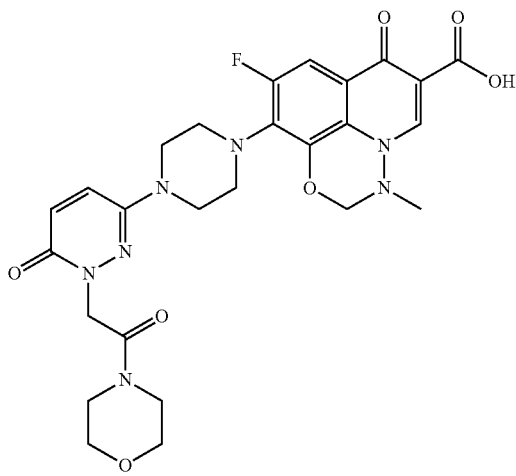

As described for compound 20a, 20d was obtained starting from 19d (877 mg, 2.85 mmol, 2.0 eq.), pyridine (6 mL), N-methylmorpholine (0.8 mL, 16.00 mmol, 5.0 eq.) and TNOC (402 mg, 1.42 mmol, 1.0 eq.). The crude product was purified by T.L.C. preparative to afford the title compound (53 mg, 7%) as a yellow solid.

HPLC (gradient 5%-80% ACN in $H_2O$): >95%

MS (ESI+) (+0.1% HCOOH): 521.20 $[C_{26}H_{28}FN_7O_7+H]^+$ (m/z)

mp=315° C.-317° C.

EXAMPLE XXVI

8-Fluoro-3-methyl-9-{4-[1-(2-morpholin-4-yl-ethyl)-6-oxo-1,6-dihydro-pyridazin-3-yl]-piperazin-1-yl}-6-oxo-2,3-dihydro-6H-1-oxa-3,3a-diaza-phenalene-5-carboxylic acid (20e)

Step A: Preparation of 18e

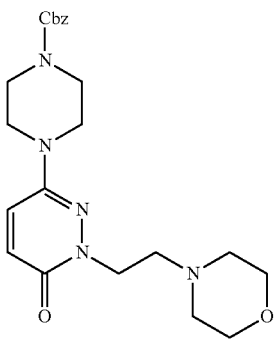

Following general procedure F, 18e was obtained starting from compound 17 g, 3.5 mmol, 1.0 eq.), 4-(2-chloroethyl)-morpholine hydrochloride (2.0 g, 10.25 mmol, 3.0 eq.) and $K_2CO_3$ (1.21 g, 8.75 mmol, 2.5 eq.). The crude product was purified by flash chromatography on silica gel, eluting with dichloromethane-methanol (99:1 to 90:10) to afford 18e (1.45 g, 97%) as a yellow solid.

Step B: Preparation of 19e

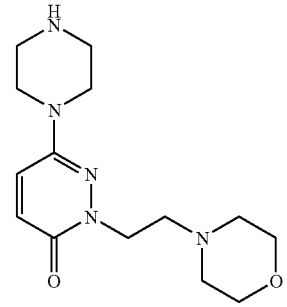

As described for compound 8a, 19e was obtained starting from 18e (1.7 g, 4.0 mmol) using Pd/C (150 mg). The crude product was purified by flash chromatography on silica gel, eluting with dichloromethane—7N $NH_3$ in methanol (95:5 to 90:10) to afford 19e (1.09 g, 94%) as a yellow solid.

MS (ESI+) (+0.1% HCOOH): 294.13 $[C_{14}H_{23}N_5O_2+H]^+$ (m/z)

Step C: Preparation of 20e

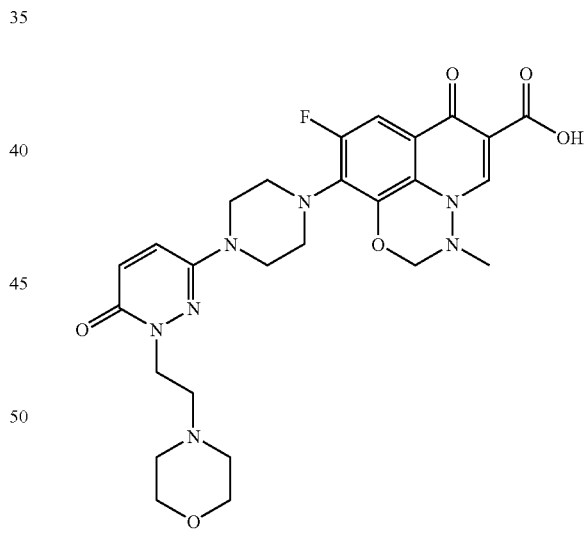

As described for compound 20a, 20e was obtained starting from 19e (1.04 g, 3.54 mmol, 2.0 eq.), pyridine (6 mL), N-methylmorpholine (1 mL, 20.0 mmol, 15.0 eq.) and TNOC (503 mg, 1.78 mmol, 1.0 eq.). The crude product was triturated with hot methanol and filtrated to afford the title compound (430 mg, 44%) as a yellow solid.

HPLC (gradient 5%-80% ACN in $H_2O$): >95%

MS (ESI+) (+0.1% HCOOH): 556.20 $[C_{26}H_{30}FN_7O_6+H]^+$ (m/z)

mp=255° C.-257° C.

Synthetic Scheme for the Preparation of Compound 25

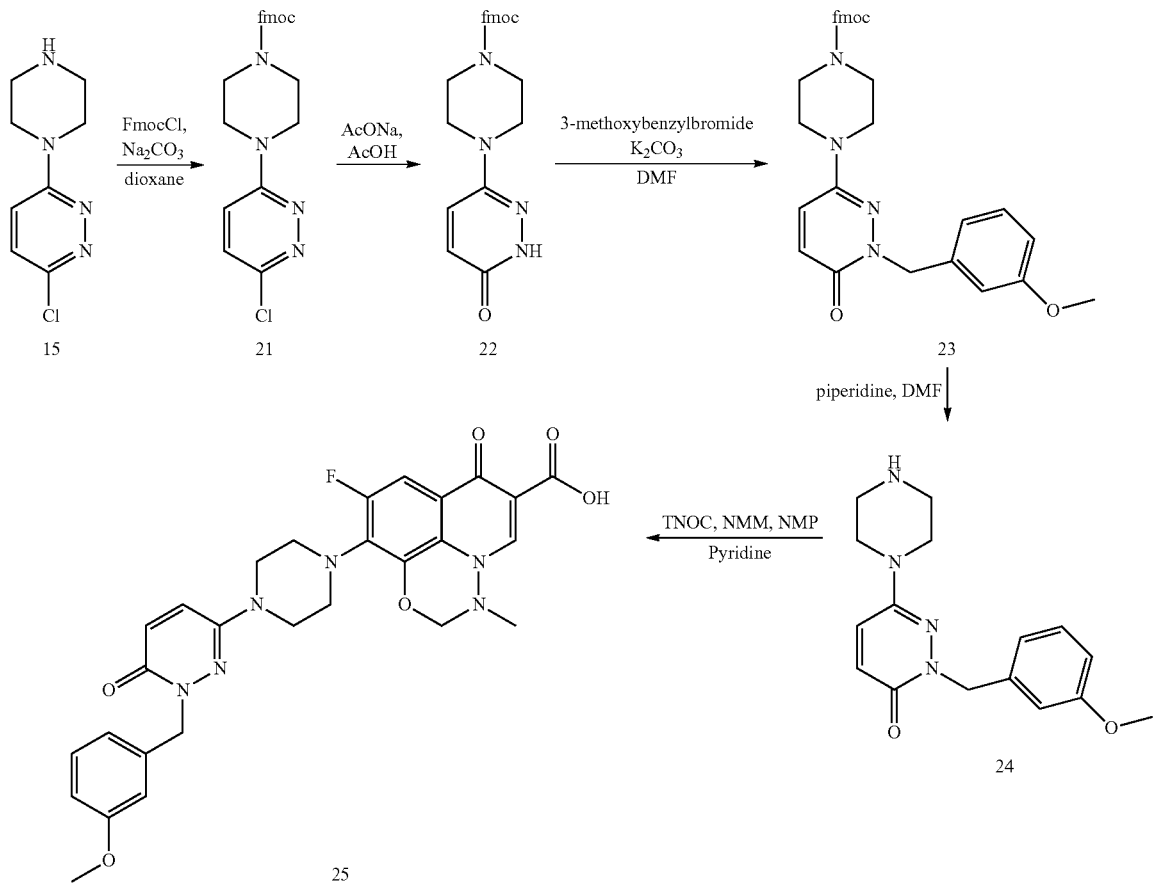

EXAMPLE XXVII

8-Fluoro-9-{4-[1-(3-methoxy-benzyl)-6-oxo-1,6-dihydro-pyridazin-3-yl]-piperazin-1-yl}-3-methyl-6-oxo-2,3-dihydro-6H-1-oxa-3,3a-diaza-phenalene-5-carboxylic acid (25)

Step A: Preparation of 21

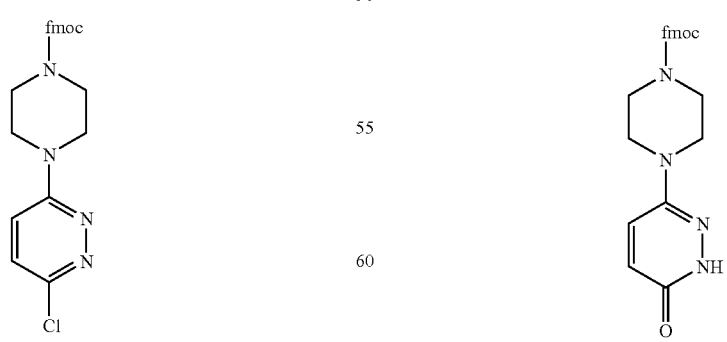

To a mixture of 15 (1.0 g, 5.0 mmol, 1.0 eq.), an aqueous solution of $Na_2CO_3$ (C=10 g/100 mL, 14 mL, 12.5 mmol, 2.5 eq.) and dioxane (14 mL) cooled to 0° C., was added dropwise FmocCl (2.0 g, 7.5 mmol, 1.5 eq.). The reaction mixture was stirred at room temperature for 18 hours. The reaction mixture was diluted with DCM, the organic phase was washed with $H_2O$ and dried over $MgSO_4$. The crude product was purified by flash chromatography on silica gel, eluting with dichloromethane-methanol (98:2 to 90:10) to afford 21 (1.90 g, 89%) as a white solid.

Step B: Preparation of 22

As described for compound 17, 22 was obtained starting from 21 (1.9 g, 4.51 mmol, 1.0 eq.) and sodium acetate (1.1 mg, 13.0 mmol, 3.0 eq.). The crude product was purified by flash chromatography on silica gel, eluting with dichloromethane-methanol (95:5) to afford 22 (1.25 g, 96%) as a yellow solid.

Step C: Preparation of 23

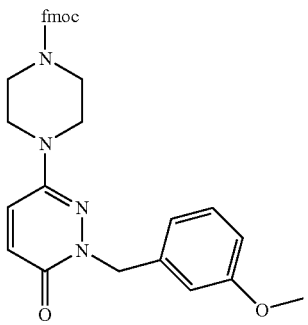

Following general procedure F, 23 was obtained starting from compound 22 (160 mg, 0.39 mmol, 1.0 eq.) and 3-methoxybenzylbromide (111 μL, 0.078 mmol, 2.0 eq.) and $K_2CO_3$ (1.10 g, 0.79 mmol, 2.0 eq.). The crude product was purified by flash chromatography on silica gel, eluting with cyclohexane-ethyl acetate (5:5 to 0:1) to afford 23 (100 mg, 48%).

Step D: Preparation of 24

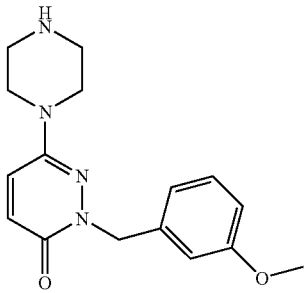

To a solution of 23 (823 mg, 1.17 mmol, 1.0 eq.) in DMF (5 mL) was added piperidine (1 mL). The reaction mixture was stirred at room temperature for 6 hours. The reaction mixture was concentrated and was purified by flash chromatography on silica gel, eluting with dichloromethane-methanol (95:5 to 80:20) to afford 24 (300 mg, 60%) as a colorless oil.

Step E: Preparation of 25

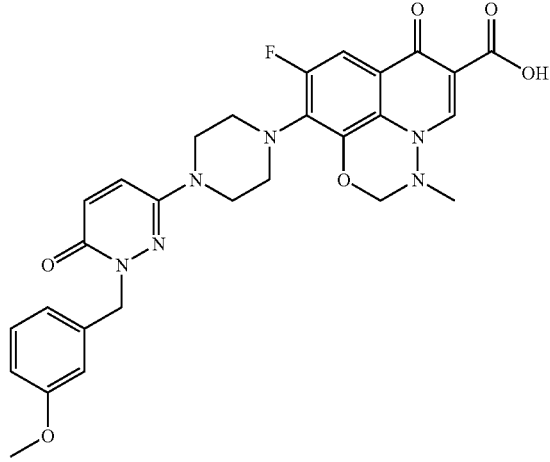

As described for compound 20a, 25 was obtained starting from 24 (300 mg, 0.99 mmol, 2.0 eq.), pyridine (4 mL,) N-methylmorpholine (0.2 mL, 4.0 mmol, 4.0 eq.) and TNOC (140 mg, 0.50 mmol, 1.0 eq.). The crude product was purified by T.L.C. preparative to afford the title compound (80 mg, 28%) as a yellow solid.

HPLC (gradient 5%-80% ACN in $H_2O$): >95%

MS (ESI+) (+0.1% HCOOH): 563.15 $[C_{28}H_{27}FN_6O_6+H]^+$ (m/z)

mp=245° C.-247° C.

Anti-Infectious Activity Test Protocol a. Aim of the Study and Choice of Strains In order to assess the anti-infectious activity, a test to determine the minimal inhibitory concentrations (MIC), of the synthesized molecules is implemented. This comparative test, using a reference fluoroquinolone, measures the minimum inhibitory concentrations for the principal reference and in-situ bacteria, isolated from human and animal pathologies (canine, feline, bovine or porcine). These bacteria represent different resistance populations vis-à-vis the fluoroquinolones for each bacterial species selected and come from Applicant's private collection or ATCC references, *M. haemolytica* (2); *B. bronchiseptica; P. aeruginosa* (2); *E. coli* (3); *S. aureus* (3); *S. uberis; M. bovis* and *bovirhinis; C. perfringens*.

b. Experimental Methodology for Determining MICs

MIC determination is carried out by microdilution in a liquid medium. The method used for the aerobic and anaerobic bacteria is based on the CLSI (NCCLS) M31-A (May 2002) guideline "Performance Standards for Antimicrobial Disk and dilution susceptibility tests for bacteria isolated from animals". The method used for the mycoplasma is based on the CLSI (NCCLS) M31-A (May 2002) guideline and the article by F. Poumarat and J. L. Martel.

For each molecule, the concentrations to be tested vis-à-vis the strains are:
either between 0.001 and 1 μg/ml
or between 0.03 and 32 pg/ml
Controls were introduced into each test.
Acceptable results of these controls validate the results obtained for each molecule.

c. Results

The results obtained for each of the molecules are summarized in table form in order to:
Assess the intrinsic performance of the molecule
Facilitate comparison between molecules
Discuss the data obtained in relation to the reference.

TABLE I

| | (MICs μg/ml) | | | | | | |
|---|---|---|---|---|---|---|---|
| Compound of example | Man hae s | Man hae r | Bor bron | Pse aer s | Pse aer r | E coli | Str ube |
| 7 | 0.03 | 4 | 0.5 | 1 | 8 | 0.06 | 0.5 |
| 6 | 0.06 | 16 | 1 | 2 | 32 | 0.12 | 1 |
| 8 | 0.03 | 8 | 0.5 | 0.5 | 8 | 0.03 | 0.5 |
| 9 | 0.03 | 4 | 0.25 | 0.5 | 8 | 0.03 | 0.5 |

| Compound of example | Sta aur s | Sta aur r | Myc bov | Clo per |
|---|---|---|---|---|
| 7 | 0.25 | 16 | 1 | 0.25 |
| 6 | 0.25 | 16 | 1 | 0.5 |
| 8 | 0.25 | 16 | 1 | 0.25 |
| 9 | 0.12 | 8 | 0.5 | 0.5 |

TABLE II

| | | | (MICs µg/ml) | | | | |
|---|---|---|---|---|---|---|---|
| Compound of example | Man hae s | Man hae r | Bor bron | Pse aer s | Pse aer r | E coli | Str ube |
| 5 | 0.25 | >1 | >1 | | | 1 | 1 |
| 2 | 0.25 | >1 | | | | >1 | 2 |
| 1 | 1 | >1 | | | | >1 | 2 |
| 4 | 0.25 | | 2 | | | >1 | 0.5 |
| 3 | 0.5 | | 2 | | | >1 | 1 |

| Compound of example | Sta aur s | Sta aur r | Myc bov | Clo per |
|---|---|---|---|---|
| 5 | 0.06 | 4 | 0.5 | <0.03 |
| 2 | 0.12 | 8 | 1 | 0.25 |
| 1 | 0.25 | 16 | 0.5 | 0.5 |
| 4 | 0.06 | 4 | 0.5 | 0.25 |
| 3 | 0.25 | 16 | 2 | 0.5 |

Names of the bacteria:
Man hae=Mannheimia haemolytica, Bor bron=Bordetella bronchiseptica, Pse aer=Pseudomonas aeruginosa, s=susceptible E. coli=Escherichia coli, Str ube=Streptococcus uberis, Sta aur=Staphylococcus aureus, Myc bov=Mycoplasma bovis, Clo per=Clostridium perfringens r=resistant

The invention claimed is:
1. The compounds of formula (I)

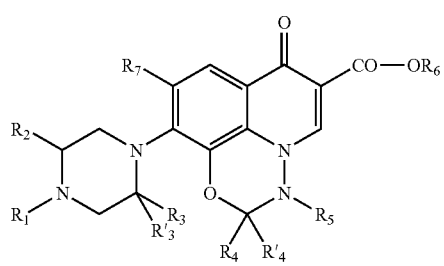

wherein:
either $R_1$ and $R_2$ form a 5 or 6 membered carbon cycle optionally substituted by a group Ra and/or by two groups Rb and R'b fixed on the same carbon atom, Ra represents hydrogen, halogen, ($C_1$-$C_6$) linear or branched alkyl, ($C_3$-$C_6$) cyclic alkyl, ($C_6$-$C_{10}$) aryl, ($C_7$-$C_{12}$) aralkyl, OH, ($C_1$-$C_6$) linear or branched alkoxy, O—($C_6$-$C_{10}$) aryl, O—($C_7$-$C_{12}$) aralkyl or NRR', R and R', represent together a ($C_3$-$C_6$) carbon chain possibly interrupted by an heteroatom selected from N, O and S and optionally substituted by 1 or 2 ($C_1$-$C_6$) linear or branched alkyls, or R and R', identical or different, represent hydrogen, ($C_1$-$C_6$) linear or branched alkyl, ($C_3$-$C_6$) cyclic alkyl or R represents hydrogen and R' represents a 5 or 6 membered heterocycle containing 1 to 3 heteroatoms selected from N, O and S, optionally substituted by 1 or 2 ($C_1$-$C_6$) linear or branched alkyls, Rb and R'b, identical or different, represent hydrogen, ($C_1$-$C_6$) linear or branched alkyl, ($C_3$-$C_6$) cyclic alkyl, ($C_6$-$C_{10}$) aryl or ($C_7$-$C_{12}$) aralkyl, or Rb and R'b form together a carbonyl;
or $R_1$ represents a CO—R'1 radical, wherein R'$_1$ represents a 5 or 6 membered aromatic heterocycle containing 1 to 3 heteroatoms selected from N, O and S, optionally substituted by 1 or 2 ($C_1$-$C_6$) linear or branched alkyls and $R_2$ represents hydrogen;
or $R_1$ represents a radical of formula:

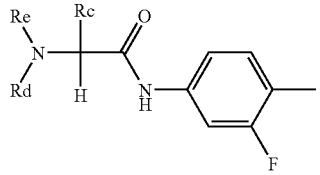

wherein Rc represents a ($C_1$-$C_6$) linear or branched alkyl, optionally substituted by a member of the group constituted by COOH, COORf, $NH_2$, NH($C_1$-$C_6$) linear or branched alkyl, N($C_1$-$C_6$) di-linear or branched alkyl and NH—CO($C_1$-$C_6$) linear or branched alkyl, Rf represents a ($C_1$-$C_6$) linear or branched alkyl, Rd represents hydrogen or CO—($C_1$-$C_6$) linear or branched alkyl and Re represents hydrogen, or Rc and Re form a pyrrolidine ring, and Rd is defined as above, and $R_2$ represents hydrogen;
or $R_1$ represents a radical of formula:

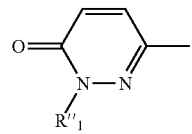

wherein R"1 represents a ($C_1$-$C_6$) linear or branched alkyl substituted by COOH, COORf, Rg or CORg, Rf is defined as above, Rg represents a morpholino, thiomorpholino or piperazino group possibly substituted by a ($C_1$-$C_6$) linear or branched alkyl, or Rg represents phenyl optionally substituted by 1 to 3 members of the group constituted by halogen, $CF_3$, ($C_1$-$C_6$) linear or branched alkyl and ($C_1$-$C_6$) linear or branched alkoxy, or Rg represents a 5 or 6 membered heterocycle containing 1 to 3 heteroatoms selected from N, O and S, optionally substituted by 1 or 2 ($C_1$-$C_6$) linear or branched alkyls, and $R_2$ represents hydrogen;
$R_3$ represents hydrogen, —$(CH_2)_m$—NRR', —$(CH_2)_m$—OR, ($C_1$-$C_6$) linear or branched alkyl, ($C_3$-$C_6$) cyclic alkyl, or $R_3$ represents ($C_6$-$C_{10}$) aryl or ($C_7$-$C_{12}$) aralkyl or a 5 or 6 membered heterocycle containing 1 to 3 heteroatoms selected from N, O and S, all being possibly substituted by halogen, $CF_3$, ($C_1$-$C_6$) linear or branched alkyl and ($C_1$-$C_6$) linear or branched alkoxy, m is 0, 1 or 2 and R and R'are defined as above and R'$_3$ represents hydrogen,
or $R_3$ and R'$_3$ represent ($C_1$-$C_6$) linear or branched alkyl or form together a ($C_3$-$C_6$) spiro ring;
$R_4$ and R'$_4$, identical or different, represent hydrogen or ($C_1$-$C_6$) linear or branched alkyl optionally substituted by 1 to 3 halogens or $R_4$ represents a ($C_1$-$C_6$) linear or branched alkoxy carbonyl group and R'$_4$ represents hydrogen;
$R_5$ represents methyl optionally substituted by one to three halogens;
$R_6$ represents hydrogen, ($C_1$-$C_6$) linear or branched alkyl or ($C_7$-$C_{12}$) aralkyl;
$R_7$ represents hydrogen, fluorine, $NO_2$, $CF_3$ or CN;
in the form of mixtures of enantiomers or single enantiomers, as well as their addition salts with mineral and organic acids and their salts with mineral or organic bases.

2. The compounds of formula (I) according to claim 1, wherein $R_4$, $R'_4$ and $R_6$ represent hydrogen, $R_5$ represents methyl, and $R_7$ represents fluorine.

3. The compounds of formula (I) according to claim 1, wherein $R_1$ and $R_2$ form a 5 or 6 membered carbon cycle optionally substituted as defined in claim 1.

4. The compounds of formula (I) according to claim 1, wherein R1 and R2 form a 5 membered carbon cycle, represented by the formula ($I_1$):

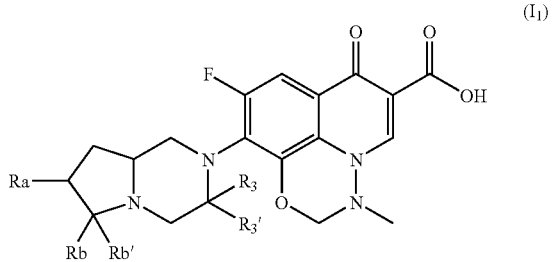

wherein Ra, Rb and R'b, $R_3$ and $R'_3$ are defined as in claim 1.

5. The compounds of formula (I) according to claim 1, wherein $R_1$ represents a CO—$R'_1$ radical, wherein $R'_1$ represents a 5 or 6 membered heterocycle containing 1 to 3 heteroatoms selected from N, O and S, optionally substituted by 1 or 2 ($C_1$-$C_6$) linear or branched alkyls, and $R_2$ represents hydrogen.

6. The compounds of formula (I) according to claim 1, wherein $R_1$ represents a radical of formula:

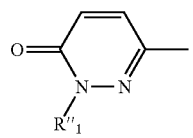

wherein $R''_1$ represents a ($C_1$-$C_6$) linear or branched alkyl radical substituted by COOH, COORf, Rg or CORg, Rf represents a ($C_1$-$C_6$) linear or branched alkyl, Rg represents morpholino, thiomorpholino or piperazino group, possibly substituted by a ($C_1$-$C_6$) linear or branched alkyl radical or Rg represents phenyl optionally substituted by 1 to 3 members of the group constituted by halogen, $CF_3$, ($C_1$-$C_6$) linear or branched alkyl and ($C_1$-$C_6$) linear or branched alkoxy, or Rg represents a 5 or 6 membered heterocycle containing 1 to 3 heteroatoms selected from N, O and S, optionally substituted by 1 or 2 ($C_1$-$C_6$) linear or branched alkyls, and $R_2$ represents hydrogen.

7. Any one of the compounds of formula (I) according to claim 1, the names of which follow:
   8-Fluoro-3-methyl-9-(octahydro-pyrido[1,2-a]pyrazin-2-yl)-6-oxo-2,3-dihydro-6H-1-oxa-3,3a-diaza-phenalene-5-carboxylic acid,
   8-Fluoro-9-(hexahydro-pyrrolo[1,2-a]pyrazin-2-yl)-3-methyl-6-oxo-2,3-dihydro-6H-1-oxa-3,3a-diaza-phenalene-5-carboxylic acid,
   8-Fluoro-9-(S)-hexahydro-pyrrolo[1,2-a]pyrazin-2-yl-3-methyl-6-oxo-2,3-dihydro-6H-1-oxa-3,3a-diaza-phenalene-5-carboxylic acid,
   8-Fluoro-9-(R)-hexahydro-pyrrolo[1,2-a]pyrazin-2-yl-3-methyl-6-oxo-2,3-dihydro-6H-1-oxa-3,3a-diaza-phenalene-5-carboxylic acid,
   8-Fluoro-3-methyl-9-[4-(1-methyl-1H-pyrrole-2-carbonyl)-piperazin-1-yl]-6-oxo-2,3-dihydro-6H-1-oxa-3,3a-diaza-phenalene-5-carboxylic acid,
   9-[4-(2,3-dihydro-thiazole-4-carbonyl)-piperazin-1-yl]-8-fluoro-3-methyl-6-oxo-2,3-dihydro-6H-1-oxa-3,3a-diaza-phenalene-5-carboxylic acid,
   8-Fluoro-3-methyl-9-[4-(4-methyl-thiazole-5-carbonyl)-piperazin-1-yl]-6-oxo-2,3-dihydro-6H-1-oxa-3,3a-diaza-phenalene-5-carboxylic acid,
   8-Fluoro-3-methyl-6-oxo-9-[4-(thiophene-2-carbonyl)-piperazin-1-yl]-2,3-dihydro-6H-1-oxa-3,3a-diaza-phenalene-5-carboxylic acid,
   8-Fluoro-9-[4-(furan-2-carbonyl)-piperazin-1-yl]-3-methyl-6-oxo-2,3-dihydro-6H-1-oxa-3,3a-diaza-phenalene-5-carboxylic acid,
   8-Fluoro-3-methyl-9-{4-[1-(2-morpholin-4-yl-ethyl)-6-oxo-1,6-dihydro-pyridazin-3-yl]-piperazin-1-yl}-6-oxo-2,3-dihydro-6H-1-oxa-3,3a-diaza-phenalene-5-carboxylic acid,
   8-Fluoro-9-{4-[1-(3-methoxy-benzyl)-6-oxo-1,6-dihydro-pyridazin-3-yl]-piperazin-1-yl}-3-methyl-6-oxo-2,3-dihydro-6H-1-oxa-3,3a-diaza-phenalene-5-carboxylic acid,
as well as their salts.

8. A method for the preparation of the compounds of formula (I) as defined in claim 1, further comprising a compound of formula (II):

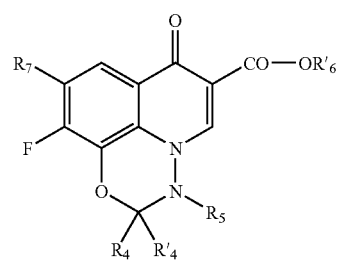

in which $R_4$, $R'_4$, $R_5$ and $R_7$ are as defined in claim 1 and $R'_6$ has the values of $R_6$ defined in claim 1 or represents another group protecting the carboxy function, is treated by a compound of formula (III):

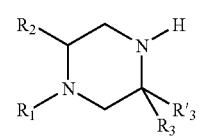

in which $R_1$, $R_2$, $R_3$ and $R'_3$ are as previously defined, in the presence of a base, then, if appropriate, the protective groups present are eliminated and, if desired, the carboxy group is esterified by action of an alcohol, and the compound of formula (I) is salified.

9. A pharmaceutical composition comprising compounds of claim 1 and a pharmaceutically acceptable carrier.

10. A pharmaceutical composition comprising compounds of claim 2 and a pharmaceutically acceptable carrier.

11. A pharmaceutical composition comprising compounds of claim 3 and a pharmaceutically acceptable carrier.

12. A pharmaceutical composition comprising compounds of claim 4 and a pharmaceutically acceptable carrier.

13. A pharmaceutical composition comprising compounds of claim 5 and a pharmaceutically acceptable carrier.

14. A pharmaceutical composition comprising compounds of claim 6 and a pharmaceutically acceptable carrier.

15. A pharmaceutical composition comprising compounds of claim 7 and a pharmaceutically acceptable carrier.

* * * * *